US012247254B2

(12) United States Patent
Vermaas et al.

(10) Patent No.: US 12,247,254 B2
(45) Date of Patent: Mar. 11, 2025

(54) COMPOSITIONS AND METHODS FOR IMPROVING SAMPLE IDENTIFICATION IN INDEXED NUCLEIC ACID LIBRARIES

(71) Applicants: Illumina, Inc., San Diego, CA (US); Illumina Cambridge Limited, Cambridge (GB)

(72) Inventors: Eric Hans Vermaas, San Diego, CA (US); Mahdieh Khosroheidari, San Diego, CA (US); Claire Bevis-Mott, Cambridge (GB)

(73) Assignees: Illumina, Inc., San Diego, CA (US); Illumina Cambridge Limited, Cambridge (GB)

( * ) Notice: Subject to any disclaimer, the term of this patent is extended or adjusted under 35 U.S.C. 154(b) by 847 days.

(21) Appl. No.: 17/181,271

(22) Filed: Feb. 22, 2021

(65) Prior Publication Data

US 2021/0172014 A1    Jun. 10, 2021

Related U.S. Application Data

(62) Division of application No. 15/959,984, filed on Apr. 23, 2018, now Pat. No. 10,934,584.

(60) Provisional application No. 62/488,833, filed on Apr. 23, 2017.

(51) Int. Cl.
| | | |
|---|---|---|
| *C12Q 1/6874* | (2018.01) | |
| *C12Q 1/6806* | (2018.01) | |
| *C12Q 1/6809* | (2018.01) | |
| *C12Q 1/6816* | (2018.01) | |
| *C12Q 1/6834* | (2018.01) | |
| *C12Q 1/6855* | (2018.01) | |
| *C40B 20/04* | (2006.01) | |
| *C40B 50/16* | (2006.01) | |
| *C40B 50/18* | (2006.01) | |
| *C40B 70/00* | (2006.01) | |
| *C40B 80/00* | (2006.01) | |

(52) U.S. Cl.
CPC ......... *C12Q 1/6874* (2013.01); *C12Q 1/6806* (2013.01); *C12Q 1/6809* (2013.01); *C12Q 1/6816* (2013.01); *C12Q 1/6834* (2013.01); *C12Q 1/6855* (2013.01); *C40B 20/04* (2013.01); *C40B 50/16* (2013.01); *C40B 50/18* (2013.01); *C40B 70/00* (2013.01); *C40B 80/00* (2013.01)

(58) Field of Classification Search
None
See application file for complete search history.

(56) References Cited

U.S. PATENT DOCUMENTS

| | | | |
|---|---|---|---|
| 6,849,404 B2 | 2/2005 | Park et al. | |
| 7,601,499 B2 | 10/2009 | Berka et al. | |
| 7,741,463 B2 | 6/2010 | Gormley et al. | |
| 8,053,192 B2 | 11/2011 | Bignell et al. | |
| 8,182,989 B2 | 5/2012 | Bignell et al. | |
| 8,822,150 B2 | 9/2014 | Bignell et al. | |
| 8,895,249 B2 | 11/2014 | Shen et al. | |
| 9,169,513 B2 | 10/2015 | Shen et al. | |
| 9,376,678 B2 | 6/2016 | Gormley et al. | |
| 9,512,478 B2 | 12/2016 | Bignell et al. | |
| 9,650,628 B2 | 5/2017 | Amorese et al. | |
| 9,758,816 B2 | 9/2017 | Shen et al. | |
| 9,850,484 B2 | 12/2017 | Joung et al. | |
| 9,968,901 B2 | 5/2018 | Head et al. | |
| 10,036,013 B2 | 7/2018 | Kim | |
| 10,167,500 B2 | 1/2019 | Becker et al. | |
| 10,174,352 B2 | 1/2019 | Arnold et al. | |
| 10,221,452 B2 | 3/2019 | Rigatti et al. | |
| 10,253,359 B2 | 4/2019 | Gormley et al. | |
| 10,287,622 B2 | 5/2019 | Belyaev | |
| 11,359,233 B2 | 6/2022 | Woodhouse et al. | |
| 2004/0209299 A1 | 10/2004 | Pinter et al. | |
| 2006/0292611 A1 | 12/2006 | Berka | |
| 2009/0233291 A1 | 9/2009 | Chen | |
| 2010/0062494 A1 | 3/2010 | Church et al. | |
| 2010/0311064 A1* | 12/2010 | Oliphant et al. ..... | C12Q 1/6834 435/91.52 |
| 2013/0231253 A1 | 9/2013 | Amorese et al. | |
| 2015/0051116 A1 | 2/2015 | Kim | |
| 2016/0186249 A1 | 6/2016 | Becker et al. | |
| 2016/0355880 A1 | 12/2016 | Gormley et al. | |
| 2018/0044668 A1 | 2/2018 | Jiang et al. | |
| 2018/0305750 A1 | 10/2018 | Smith et al. | |
| 2018/0305751 A1 | 10/2018 | Vermaas et al. | |

(Continued)

FOREIGN PATENT DOCUMENTS

| | | |
|---|---|---|
| EP | 1256630 A2 | 11/2002 |
| EP | 1256630 | 2/2004 |
| EP | 1256630 A3 | 2/2004 |

(Continued)

OTHER PUBLICATIONS

Zheng et al., "Titration-free 454 sequencing using Y adapters," Nat. Protoc. 2011, 6:1367-1376. (Year: 2011).*

Ambadar et al., "High Throughput Sequencing: An Overview of Sequencing Chemistry" Indian J Microbiol, Jul. 2016;56(4):394-404.

International Search Report and Written Opinion for International Patent Application No. PCT/IB2018/000497 mailed Jun. 29, 2018, 14 pages.

International Search Report and Written Opinion for International Patent Application No. PCT/IB2018/000509, mailed Sep. 12, 2018, 14 pages.

(Continued)

*Primary Examiner* — Kaijiang Zhang

(74) *Attorney, Agent, or Firm* — Illumina, Inc.

(57) ABSTRACT

The present invention is concerned with compositions and methods for improving the rate of correct sample identification in indexed nucleic acid library preparations for multiplex next generation sequencing by modifying or blocking 5' and 3' ends of pooled indexed polynucleotides from multiple samples, with an optional exonuclease treatment, prior to amplification and sequencing.

17 Claims, 9 Drawing Sheets

(56) References Cited

U.S. PATENT DOCUMENTS

| | | | |
|---|---|---|---|
| 2018/0305752 A1 | 10/2018 | Vermaas et al. | |
| 2018/0305753 A1 | 10/2018 | Chesney et al. | |

FOREIGN PATENT DOCUMENTS

| | | | |
|---|---|---|---|
| GB | 20160015486 | | 10/2016 |
| WO | 052006 | | 5/2007 |
| WO | 2007052006 | A1 | 5/2007 |
| WO | 2009098037 | A1 | 8/2009 |
| WO | 112534 | | 9/2011 |
| WO | 177220 | | 11/2013 |
| WO | 2013177220 | A1 | 11/2013 |
| WO | 2015/069374 | A1 | 5/2015 |
| WO | 069374 | | 5/2015 |
| WO | WO 2016/058517 | A1 | 4/2016 |
| WO | 130704 | | 8/2016 |
| WO | 2018144216 | A1 | 8/2018 |
| WO | 197945 | | 11/2018 |
| WO | 0197950 | | 11/2018 |
| WO | 200380 | | 11/2018 |
| WO | 20180200386 | | 11/2018 |

OTHER PUBLICATIONS

International Search Report and Written Opinion for International Patent Application No. PCT/US2018/028867, mailed Jun. 28, 2018, 15 pages.

International Search Report and Written Opinion for International Patent Application No. PCT/US2018/028881, mailed Jun. 28, 2018, 14 pages.

"Effects of Index Misassignment on Multiplexing and Downstream Analysis," Illumina, Inc., 2017, 4 pages.

Esling et al., "Accurate multiplexing and filtering for high-throughput amplicon-sequencing," Nucleic Acids Research, Mar. 11, 2015, Epub Feb. 17, 2015; 43(5):2513-2524.

Kircher et al., "Double indexing overcomes inaccuracies in multi-plex sequencing on the Illumina platform," Nucleic Acids Research, Jan. 1, 2012, Epub Oct. 21, 2011; XP002751968, 40(1):e3-1, 8 pages.

Kircher et al., "Double indexing overcomes inaccuracies in multi-plex sequencing on the Illumina platform," Nucleic Acids Research, Supplementary Tables, Jan. 1, 2012, Epub Oct. 21, 2011; XP055476349, 40(1):e3-e3, 17 pages.

Sinha et al., "Index switching causes "spreading-of-signal" among multiplexed samples in Illumina HiSeq 4000 DNA sequencing," bioRxiv, Apr. 9, 2017, XP055483189, 29 pages.

European Partial Search Report for Appl. No. 21183272.0-1118, dated Oct. 20, 2021, 9 pages.

Kircher, et al. "Double indexing overcomes inaccuracies in multi-plex sequencing on the Illumina platform", Nucleic Acids Research, vol. 40, No. 1, Jan. 1, 2012, XP055476349.

Nikiforov et al., "The Use of Phosphorothioate Primers and Exonuclease Hydrolosis for the Preparation of Single-stranded PCR Products and their Detection by Solid-phase Hybridization," Jan. 30, 2012, *Genome Research*, 3:285-94.

* cited by examiner 12 different P7 Indices; 8 different P5 Indices

COMPOSITIONS AND METHODS FOR IMPROVING SAMPLE IDENTIFICATION IN INDEXED NUCLEIC ACID LIBRARIES

RELATED APPLICATION

This application is a divisional application of U.S. patent application Ser. No. 15/959,984, pending, filed 23 Apr. 2018, which claims the benefit of U.S. Provisional Application No. 62/488,833, filed on Apr. 23, 2017, which application is hereby incorporated herein by reference.

FIELD

The present disclosure relates to, among other things, sequencing of polynucleotides from multiple libraries; and more particularly to increasing the likelihood that sequencing properly identifies the library from which the polynucleotides originated.

BACKGROUND

Improvements in sequencing methodologies have allowed for sequencing of pooled or multiplexed polynucleic acids from different libraries in a single sequencing protocol. A library-specific sequence (an "index tag") may be added to polynucleic acids of each library so that the origin of each sequenced polynucleic acid may be properly identified. The index tag sequence may be added to polynucleic acids of a library by, for example, ligating adapters comprising the index tag sequence to ends of the polynucleic acids.

The adapters may contain sequences in addition to the index tag sequence, such as a universal extension primer sequence and a universal sequencing primer sequence. The universal extension primer sequence may, among other things, hybridize to a first oligonucleotide coupled to a solid surface. The first oligonucleotide may have a free 3' end from which a polymerase may add nucleotides to extend the sequence using the hybridized library polynucleotide as a template, resulting in a reverse strand of the library polynucleotide being coupled to the solid surface. Additional copies of forward and reverse strands may be coupled to the solid surface through cluster amplification. One example of cluster amplification is bridge amplification in which the 3' end of previously amplified polynucleotides that are bound to the solid surface hybridize to second oligonucleotides bound to the solid surface. The second oligonucleotide may have a free 3' end from which a polymerase may add nucleotides to extend the sequence using the coupled reverse strand polynucleotide as a template, resulting in a forward strand of the library polynucleotide being coupled to the solid surface via the second oligonucleotide. The process may be repeated to produce clusters of forward and reverse strands coupled to the solid surface. The forward strands or the reverse strands may be removed, e.g. via cleavage, prior to sequencing.

A sequencing primer may hybridize to a portion of a polynucleotide strand coupled to the solid support. For example, the sequencing primer may hybridize to a universal sequencing primer sequence, if present. Sequencing may occur through multiple rounds of addition of nucleotides to the sequencing primer using the coupled polynucleotide as a template, and detecting the identity of the added nucleotides. Hybridization of the sequencing primer may occur at a location on the coupled polynucleotide strand to allow sequence identification of the index tag sequence as well as a target sequence of the polynucleotide coupled to the solid surface or separate sequencing primers may be employed to separately sequence the index tag sequence and the target sequence. Accordingly, the target sequence may be indexed to a particular library of origin based on the index tag sequence associated with the target sequence.

Despite the inclusion of a library-specific index tag sequence to each polynucleic acid to be sequenced, errors in identifying the library origin of a sequenced polynucleic acid may occur due to a phenomenon known as index hopping. Index hopping occurs when index tag sequences from one library are inadvertently added to a polynucleic acid from a different library. Index hopping may occur during library preparation or cluster amplification of the polynucleotides on a flow cell or other suitable solid support for sequencing. Index hopping may confound results of sequencing, such as resulting in improper assignment of library origin of a sequenced polynucleotide or discarding sequencing results.

BRIEF SUMMARY

One or more aspects of the present disclosure address at least one potential mechanism associated with index hopping by blocking 3' ends of polynucleic acids, including unincorporated adapters, during library sample preparation. Without intending to be bound by theory, it is believed that index hopping may occur when an unincorporated adapter comprising an index tag sequence for one library hybridizes to a portion of an adapter from another library, and the unincorporated adapter serves as a primer during cluster amplification. Thus, a target sequence from one library may be tagged with an index tag of an adapter from another library. During subsequent rounds of cluster amplification, additional copies of the miss-tagged target may be amplified prior to sequencing. Such index hopping may confound results of subsequent sequencing. By blocking the 3' ends of polynucleotides in a library, including unincorporated adapters, during library sample preparation, the ability of the unincorporated adapters to serve as primers during cluster amplification will be blocked.

In addition or alternatively, aspects of embodiments of the present disclosure relates to protecting from exonucleases the 5' and 3' ends of template polynucleotides for immobilizing on a surface for sequencing, and degrading residual unprotected polynucleotides to inhibit the ability of the unprotected polynucleotides from participating in index hopping.

In some aspects described herein, a method includes providing a first library comprising a first plurality of polynucleotides having a first adapter-target-first adapter sequence. The polynucleotides of the first plurality of polynucleotide are double stranded in a region comprising the target and at least a portion of the first adapter on both ends of the target. The method further includes providing a first primer oligonucleotide configured to hybridize with a portion of the first adapter in proximity to a 3' end of a strand of the first adapter. The 5' end of the first primer oligonucleotide is modified to prevent digestion by an enzyme having 5' exonuclease activity. The method further includes providing a second primer oligonucleotide configured to hybridize with a complement of a portion of the first adapter in proximity to a 3' end of a strand of the complement of the first adapter. The 5' end of the second primer oligonucleotide is modified to prevent digestion by an enzyme having 5' exonuclease activity. The method further includes incubating the first library with the first and second primer oligonucleotides in a solution under conditions suitable to amplify the polynucleotides having a first adapter-target-first adapter sequence to produce an amplified first library of polynucleotides having 5' ends modified to prevent digestion by an enzyme having 5' exonuclease activity. The amplified polynucleotides have an amplified first adapter-target-amplified first adapter sequence. The amplified first adapter sequence comprises a first library-specific sequence. The method further includes modifying 3' ends of the amplified first library polynucleotides to prevent one or both of (i) digestion by an enzyme having 3' exonuclease activity, or (ii) addition of nucleotides to the 3' end by an enzyme having polymerase activity, thereby generating a protected first library of polynucleotides having modified 5' and 3' ends. Preferably, the 3' ends are modified to inhibit the addition of nucleotides to the 3' end by an enzyme having polymerase activity.

The protected first library of polynucleotides having modified 5' and 3' ends may be pooled with similar polynucleotides from other libraries and immobilized for a surface for sequencing. When the 3' ends were modified to include dideoxynucleotides, a decrease in index hopping of nearly 100-fold was observed.

In some aspects described herein, a polynucleotide prepared for immobilizing for sequencing has an adapter-target-adapter sequence. The adapter sequence comprises a library specific sequence. The polynucleotide is double stranded in a region comprising the target and at least a portion of the adapter on both ends of the target. The, 5' and 3' ends of the polynucleotide in a region of the adapter sequence are single stranded. The 5' ends are modified to prevent digestion by an enzyme having 5' exonuclease activity. The 3' ends are modified to inhibit one or both of (i) digestion by an enzyme having 3' exonuclease activity, or (ii) addition of nucleotides to the 3' end by an enzyme having polymerase activity. Preferably, the 3' ends are modified to inhibit the addition of nucleotides to the 3' end by an enzyme having polymerase activity.

In some embodiments, compositions comprise the polynucleotide and an exonuclease.

The methods, polynucleotides and compositions described herein may be useful in mitigating index hopping, for example by blocking 3' ends of polynucleotides, including unincorporated adapters, or degrading unblocked polynucleotides, including unincorporated adapters, during library sample preparation. By blocking the 3' ends of the unincorporated adapters, the unincorporated adapters cannot be extended during cluster amplification if the adapters hybridize to an adapter-target-adapter polynucleotide sequence during cluster amplification. In addition or alternatively, those polynucleotides that are not blocked at the 3' end may be degraded by an exonuclease to mitigate index hopping.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure may be best understood when read in conjunction with the following drawings.

FIG. 7A shows how reads from a given sample are incorrectly demultiplexed and mixed with a different sample following demultiplexing. FIG. 7B demonstrates index hopping in a dual index system, where it leads to unexpected combinations of index tag sequences.

FIGS. 8A and 8B illustrate the general approach to measuring the rate of index hopping in a given system. FIG. 8A shows an exemplary layout of a dual adapter plate, wherein each individual well of a 96-well plate contains a unique pair of index tag sequences.

FIG. 8B shows an experimental setup aimed at measuring the rate of index hopping, wherein only unique dual index tag combinations are used.

FIG. 9A shows a 6-fold increase in index hopping associated with a 50% spike-in of free adapters. FIG. 9B shows an approximately linear effect of the free forked adapter on the rate of index hopping within the range tested.

Figure 1:
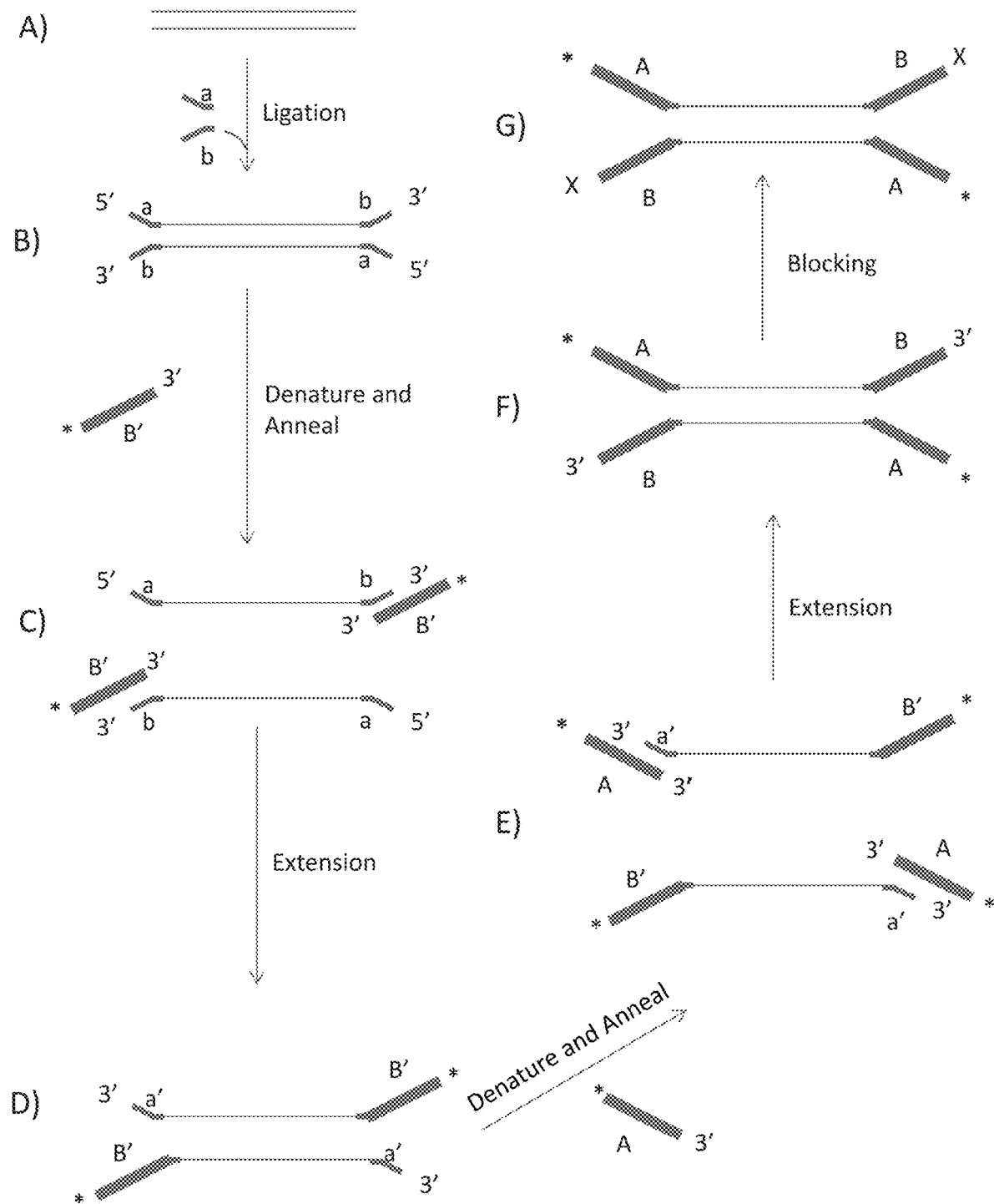
FIG. 1 is a schematic drawing illustrating an embodiment of a process for producing 5' modified and 3' blocked template polynucleotides.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Reference will now be made in greater detail to various embodiments of the subject matter of the present disclosure, some embodiments of which are illustrated in the accompanying drawings.

Definitions

All scientific and technical terms used herein have meanings commonly used in the art unless otherwise specified. The definitions provided herein are to facilitate understanding of certain terms used frequently herein and are not meant to limit the scope of the present disclosure.

As used herein, singular forms "a," "an" and "the" include plural referents unless the context clearly dictates otherwise. Thus, for example, reference to an "index tag sequence" includes examples having two or more such "index tag sequences" unless the context clearly indicates otherwise.

As used in this specification and the appended claims, the term "or" is generally employed in its sense including "and/or" unless the content clearly dictates otherwise. The term "and/or" means one or all of the listed elements or a combination of any two or more of the listed elements. The use of "and/or" in some instances does not imply that the use of "or" in other instances may not mean "and/or."

As used herein, "have", "has", "having", "include", "includes", "including", "comprise", "comprises", "comprising" or the like are used in their open ended inclusive sense, and generally mean "include, but not limited to", "includes, but not limited to", or "including, but not limited to".

"Optional" or "optionally" means that the subsequently described event, circumstance, or component, can or cannot occur, and that the description includes instances where the event, circumstance, or component, occurs and instances where it does not.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the inventive technology.

Also herein, the recitations of numerical ranges by endpoints include all numbers subsumed within that range (e.g., 1 to 5 includes 1, 1.5, 2, 2.75, 3, 3.80, 4, 5, etc.). Where a range of values is "greater than", "less than", etc. a particular value, that value is included within the range.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim may be combined or permuted with any other recited feature or aspect in any other claim or claims.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a polynucleotide comprising an adapter-target-adapter sequence includes embodiments where the polynucleotide consists of the adapter-target-adapter sequence and embodiments where the polynucleotide consists essentially of the adapter-target-adapter sequence.

As used herein, "providing" in the context of a polynucleotide, composition or article means making the polynucleotide, composition, or article, purchasing the polynucleotide, composition or article, or otherwise obtaining the compound, composition or article.

As used herein, "amplify", "amplifying" or "amplification reaction" and their derivatives, refer generally to any action or process whereby at least a portion of a polynucleotide (e.g., template polynucleotide) is replicated or copied into at least one additional polynucleotide. The additional polynucleotide optionally includes a sequence that is substantially identical or substantially complementary to at least some portion of the template polynucleotide. The template polynucleotide may be single-stranded or double-stranded and the additional polynucleotide may independently be single-stranded or double-stranded. Amplification optionally includes linear or exponential replication of a polynucleotide. In some embodiments, such amplification may be performed using isothermal conditions; in other embodiments, such amplification may include thermocycling. In some embodiments, the amplification is a multiplex amplification that includes the simultaneous amplification of a plurality of target sequences in a single amplification reaction. In some embodiments, "amplification" includes amplification of at least some portion of DNA and RNA based nucleic acids alone, or in combination. The amplification reaction may include any of the amplification processes known to one of ordinary skill in the art. In some embodiments, the amplification reaction includes polymerase chain reaction (PCR).

As used herein, the term "polymerase" is intended to be consistent with its use in the art and includes, for example, an enzyme that produces a complementary replicate of a polynucleotide using the polynucleotide as a template strand. Typically, DNA polymerases bind to the template strand and then move down the template strand sequentially adding nucleotides to the free hydroxyl group at the 3' end of a growing strand of nucleic acid. DNA polymerases typically synthesize complementary DNA molecules from DNA templates and RNA polymerases typically synthesize RNA molecules from DNA templates (transcription). Polymerases may use a short RNA or DNA strand, called a primer, to begin strand growth. Some polymerases may displace the strand upstream of the site where they are adding bases to a chain. Such polymerases are said to be strand displacing, meaning they have an activity that removes a complementary strand from a template strand being read by the polymerase. Exemplary polymerases having strand displacing activity include, without limitation, the large fragment of Bst (*Bacillus stearothermophilus*) polymerase, exo-Klenow polymerase or sequencing grade T7 exo-polymerase. Some polymerases degrade the strand in front of them, effectively replacing it with the growing chain behind (5' exonuclease activity). Some polymerases have an activity that degrades the strand behind them (3' exonuclease activity). Some useful polymerases have been modified, either by mutation or otherwise, to reduce or eliminate 3' and/or 5' exonuclease activity.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some embodiments, the plexy may be about 12-plex, 24-plex, 48-plex, 96-plex, 192-plex, 384-plex, 768-plex, 1536-plex, 3072-plex, 6144-plex or higher. It is also possible to detect the amplified target sequences by several different methodologies (e.g., gel electrophoresis followed by densitometry, quantitation with a bioanalyzer or quantitative PCR, hybridization with a labeled probe; incorporation of biotinylated primers followed by avidin-enzyme conjugate detection; incorporation of 32P-labeled deoxynucleotide triphosphates into the amplified target sequence).

As used herein, the term "primer" and its derivatives refer generally to any polynucleotide that may hybridize to a target sequence of interest. Typically, the primer functions as a substrate onto which nucleotides may be polymerized by a polymerase; in some embodiments, however, the primer may become incorporated into the synthesized nucleic acid strand and provide a site to which another primer may hybridize to prime synthesis of a new strand that is complementary to the synthesized nucleic acid molecule. The primer may be comprised of any combination of nucleotides or analogs thereof. In some embodiments, the primer is a single-stranded oligonucleotide or polynucleotide. The terms "polynucleotide" and "oligonucleotide" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). As used herein, "amplified target sequences" and its derivatives, refers generally to a polynucleotide sequence produced by the amplifying the target sequences using target-specific primers and the methods provided herein. The amplified target sequences may be either of the same sense (i.e the positive strand) or antisense (i.e., the negative strand) with respect to the target sequences.

As used herein, the terms "ligating", "ligation" and their derivatives refer generally to the process for covalently linking two or more molecules together, for example covalently linking two or more polynucleotides to each other. In some embodiments, ligation includes joining nicks between adjacent nucleotides of polynucleotides. In some embodiments, ligation includes forming a covalent bond between an end of a first and an end of a second polynucleotide. In some embodiments, the ligation may include forming a covalent bond between a 5' phosphate group of one nucleic acid and a 3' hydroxyl group of a second nucleic acid thereby forming a ligated polynucleotide. Generally for the purposes of this disclosure, an amplified target sequence may be ligated to an adapter to generate an adapter-ligated amplified target sequence.

As used herein, "ligase" and its derivatives, refers generally to any agent capable of catalyzing the ligation of two substrate molecules. In some embodiments, the ligase includes an enzyme capable of catalyzing the joining of nicks between adjacent nucleotides of a nucleic acid. In some embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases may include, but not limited to, T4 DNA ligase, T4 RNA ligase, and E. coli DNA ligase.

As used herein, "ligation conditions" and its derivatives, generally refers to conditions suitable for ligating two molecules to each other. In some embodiments, the ligation conditions are suitable for sealing nicks or gaps between nucleic acids. As used herein, the term nick or gap is consistent with the use of the term in the art. Typically, a nick or gap may be ligated in the presence of an enzyme, such as ligase at an appropriate temperature and pH. In some embodiments, T4 DNA ligase may join a nick between nucleic acids at a temperature of about 70-72° C.

As used herein, the term "universal sequence" refers to a region of sequence that is common to two or more nucleic acid molecules where the molecules also have regions of sequence that differ from each other. A universal sequence that is present in different members of a collection of molecules may allow capture of multiple different nucleic acids using a population of universal capture nucleic acids that are complementary to the universal sequence. Similarly, a universal sequence present in different members of a collection of molecules may allow the replication or amplification of multiple different nucleic acids using a population of universal primers that are complementary to the universal sequence. Thus a universal capture polynucleotide or a universal primer includes a sequence that may hybridize specifically to a universal sequence. Polynucleotides may be modified to attach universal adapters, for example, at one or both ends of the different sequences.

Index Hopping

This disclosure relates to, among other things, sequencing of nucleic acids from multiple indexed libraries; and more particularly to increasing the likelihood that sequencing properly identifies the library from which the nucleic acids originated.

When polynucleotides from different libraries are pooled or multiplexed for sequencing, the polynucleotides from each library may be modified to include a library-specific index tag sequence. During sequencing the index tag is sequenced along with target polynucleotide sequences from the libraries. Accordingly, the index tag sequence may be associated with target polynucleotide sequence so that the library from which the target sequence originated may be identified.

However, a phenomenon referred to as index hopping may occur in a small percentage of sequence results (typically 0.5% to 2%). Index hopping refers to an index tag sequence from one library being associated with target polynucleotide from another library (see FIGS. 7A and 7B). While the mechanisms by which index hopping may occur are not fully understood, the rate of index hopping may be effectively reduced by blocking the 3' end of unincorporated adapters after the adapters are attached to the target polynucleotides of a library to, among other things, attach the index tag sequence to the polynucleotide.

Initial Library Sample Preparation

Libraries comprising polynucleotides may be prepared in any suitable manner to attach oligonucleotide adapters to target polynucleotides. As used herein, a "library" is a population of polynucleotides from a given source or sample. A library comprises a plurality of target polynucleotides. As used herein, a "target polynucleotide" is a polynucleotide that is desired to sequence. The target polynucleotide may be essentially any polynucleotide of known or unknown sequence. It may be, for example, a fragment of genomic DNA or cDNA. Sequencing may result in determination of the sequence of the whole, or a part of the target polynucleotides. The target polynucleotides may be derived from a primary polynucleotide sample that has been randomly fragmented. The target polynucleotides may be processed into templates suitable for amplification by the placement of universal primer sequences at the ends of each target fragment. The target polynucleotides may also be obtained from a primary RNA sample by reverse transcription into cDNA.

The terms "polynucleotide" and "oligonucleotide" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). The terms polynucleotide and oligonucleotide used herein also encompasses cDNA, that is complementary or copy DNA produced from an RNA template, for example by the action of reverse transcriptase.

Primary polynucleotide molecules may originate in double-stranded DNA (dsDNA) form (e.g. genomic DNA fragments, PCR and amplification products and the like) or may have originated in single-stranded form, as DNA or RNA, and been converted to dsDNA form. By way of example, mRNA molecules may be copied into double-stranded cDNAs using standard techniques well known in the art. The precise sequence of primary polynucleotides is generally not material to the disclosure presented herein, and may be known or unknown.

In some embodiments, the primary target polynucleotides are RNA molecules. In an aspect of such embodiments, RNA isolated from specific samples is first converted to double-stranded DNA using techniques known in the art. The double-stranded DNA may then be index tagged with a library specific tag. Different preparations of such double-stranded DNA comprising library specific index tags may be generated, in parallel, from RNA isolated from different sources or samples. Subsequently, different preparations of double-stranded DNA comprising different library specific index tags may be mixed, sequenced en masse, and the identity of each sequenced fragment determined with respect to the library from which it was isolated/derived by virtue of the presence of a library specific index tag sequence.

In some embodiments, the primary target polynucleotides are DNA molecules. For example, the primary polynucleotides may represent the entire genetic complement of an organism, and are genomic DNA molecules, such as human DNA molecules, which include both intron and exon sequences (coding sequence), as well as non-coding regulatory sequences such as promoter and enhancer sequences. Although it could be envisaged that particular sub-sets of polynucleotide sequences or genomic DNA could also be used, such as, for example, particular chromosomes or a portion thereof. In many embodiments, the sequence of the primary polynucleotides is not known. The DNA target polynucleotides may be treated chemically or enzymatically either prior to, or subsequent to a fragmentation processes, such as a random fragmentation process, and prior to, during, or subsequent to the ligation of the adaptor oligonucleotides.

Preferably, the primary target polynucleotides are fragmented to appropriate lengths suitable for sequencing. The target polynucleotides may be fragmented in any suitable manner. Preferably, the target polynucleotides are randomly fragmented. Random fragmentation refers to the fragmentation of a polynucleotide in a non-ordered fashion by, for example, enzymatic, chemical or mechanical means. Such fragmentation methods are known in the art and utilize standard methods (Sambrook and Russell, Molecular Cloning, A Laboratory Manual, third edition). For the sake of clarity, generating smaller fragments of a larger piece of polynucleotide via specific PCR amplification of such smaller fragments is not equivalent to fragmenting the larger piece of polynucleotide because the larger piece of polynucleotide remains in intact (i.e., is not fragmented by the PCR amplification). Moreover, random fragmentation is designed to produce fragments irrespective of the sequence identity or position of nucleotides comprising and/or surrounding the break.

In some embodiments, the random fragmentation is by mechanical means such as nebulization or sonication to produce fragments of about 50 base pairs in length to about 1500 base pairs in length, such as 50-700 base pairs in length or 50-500 base pairs in length.

Fragmentation of polynucleotide molecules by mechanical means (nebulization, sonication and Hydroshear for example) may result in fragments with a heterogeneous mix of blunt and 3'- and 5'-overhanging ends. Fragment ends may be repaired using methods or kits (such as the Lucigen DNA terminator End Repair Kit) known in the art to generate ends that are optimal for insertion, for example, into blunt sites of cloning vectors. In some embodiments, the fragment ends of the population of nucleic acids are blunt ended. The fragment ends may be blunt ended and phosphorylated. The phosphate moiety may be introduced via enzymatic treatment, for example, using polynucleotide kinase.

In some embodiments, the target polynucleotide sequences are prepared with single overhanging nucleotides by, for example, activity of certain types of DNA polymerase such as Taq polymerase or Klenow exo minus polymerase which has a non-template-dependent terminal transferase activity that adds a single deoxynucleotide, for example, deoxyadenosine (A) to the 3' ends of, for example, PCR products. Such enzymes may be utilized to add a single nucleotide 'A' to the blunt ended 3' terminus of each strand of the target polynucleotide duplexes. Thus, an 'A' could be added to the 3' terminus of each end repaired duplex strand of the target polynucleotide duplex by reaction with Taq or Klenow exo minus polymerase, while the adaptor polynucleotide construct could be a T-construct with a compatible 'T' overhang present on the 3' terminus of each duplex region of the adapter construct. This end modification also prevents self-ligation of the target polynucleotides such that there is a bias towards formation of the combined ligated adapter-target polynucleotides.

In some embodiments, fragmentation is accomplished through tagmentation as described in, for example, International Patent Application Publication WO 2016/130704. In such methods transposases are employed to fragment a double stranded polynucleotide and attach a universal primer sequence into one strand of the double stranded polynucleotide. The resulting molecule may be gap-filled and subject to extension, for example by PCR amplification, using primers that comprise a 3' end that hybridizes to the attached universal primer sequence and a 5' end that contains other sequences of an adapter or using primers that comprise a 3' end that hybridizes to a complement of the attached universal primer sequence and a 5' end that contains other sequences of an adapter.

The adapters or portions of the adapters may be attached to the target polynucleotide in any other suitable manner. In some embodiments, the adapters are introduced in a multi-step process, such as a two-step process, involving ligation of a portion of the adapter to the target polynucleotide having a universal primer sequence. The second step comprises extension, for example by PCR amplification, using primers that comprise a 3' end that hybridizes to the attached universal primer sequence (or that hybridizes to a complement of the universal primer sequence) and a 5' end that contains other sequences of an adapter. By way of example, such extension may be performed as described in U.S. Pat. No. 8,053,192. Additional extensions may be performed to provide additional sequences to the 5' end of the resulting previously extended polynucleotide.

In some embodiments, the entire adapter is ligated to the fragmented target polynucleotide. The ligated adapter comprises a double stranded region that is ligated to a double stranded target polynucleotide. Preferably, the double-stranded region is as short as possible without loss of function. In this context, "function" refers to the ability of the double-stranded region to form a stable duplex under standard reaction conditions. In some embodiments, standard reactions conditions refer to reaction conditions for an enzyme-catalyzed polynucleotide ligation reaction, which will be well known to the skilled reader (e.g. incubation at a temperature in the range of 4° C. to 25° C. in a ligation buffer appropriate for the enzyme), such that the two strands forming the adaptor remain partially annealed during ligation of the adaptor to a target molecule. Ligation methods are known in the art and may utilize standard methods (Sambrook and Russell, Molecular Cloning, A Laboratory Manual, third edition). Such methods utilize ligase enzymes such as DNA ligase to effect or catalyze joining of the ends of the two polynucleotide strands of, in this case, the adapter duplex oligonucleotide and the target polynucleotide duplexes, such that covalent linkages are formed. The adaptor duplex oligonucleotide may contain a 5'-phosphate moiety in order to facilitate ligation to a target polynucleotide 3'-OH. The target polynucleotide may contain a 5'-phosphate moiety, either residual from the shearing process, or added using an enzymatic treatment step, and has been end repaired, and optionally extended by an overhanging base or bases, to give a 3'-OH suitable for ligation. In this context, attaching means covalent linkage of polynucleotide strands which were not previously covalently linked. In a particular aspect of the invention, such attaching takes place by formation of a phosphodiester linkage between the two polynucleotide strands, but other means of covalent linkage (e.g. non-phosphodiester backbone linkages) may be used. Ligation of adapters to target polynucleotides is described in more detail in, for example, U.S. Pat. No. 8,053,192.

Whether the entire adapter or a portion of the adapter is attached to the double stranded target fragment, the adapter or portion comprises a double stranded region and a region comprising two non-complementary single strands. The double-stranded region of the adapter may be of any suitable number of base pairs. Preferably, the double stranded region is a short double-stranded region, typically comprising 5 or more consecutive base pairs, formed by annealing of two partially complementary polynucleotide strands. This "double-stranded region" of the adapter refers to a region in which the two strands are annealed and does not imply any particular structural conformation. In some embodiments, the double stranded region comprises 20 or less consecutive base pairs, such as 10 or less or 5 or less consecutive base pairs.

The stability of the double-stranded region may be increased, and hence its length potentially reduced, by the inclusion of non-natural nucleotides which exhibit stronger base-pairing than standard Watson-Crick base pairs. Preferably, the two strands of the adaptor are 100% complementary in the double-stranded region.

When the adapter is attached to the target polynucleotide, the non-complementary single stranded region may form the 5' and 3' ends of the polynucleotide to be sequenced. The term "non-complementary single stranded region" refers to a region of the adapter where the sequences of the two polynucleotide strands forming the adaptor exhibit a degree of non-complementarity such that the two strands are not capable of fully annealing to each other under standard annealing conditions for a PCR reaction.

The non-complementary single stranded region is provided by different portions of the same two polynucleotide strands which form the double-stranded region. The lower limit on the length of the single-stranded portion will typically be determined by function of, for example, providing a suitable sequence for binding of a primer for primer extension, PCR and/or sequencing. Theoretically there is no upper limit on the length of the unmatched region, except that in general it is advantageous to minimize the overall length of the adaptor, for example, in order to facilitate separation of unbound adapters from adapter-target constructs following the attachment step or steps. Therefore, it is generally preferred that the non-complementary single-stranded region of the adapter is 50 or less consecutive nucleotides in length, such as 40 or less, 30 or less, or 25 or less consecutive nucleotides in length.

After the adapters or portions of the adapters are attached to the target polynucleotides, the resulting polynucleotides may be subjected to a clean-up process to enhance the purity to the adapter-target-adapter polynucleotides by removing at least a portion of the unincorporated adapters. Any suitable clean-up process may be used, such as electrophoresis, size exclusion chromatography, or the like. In some embodiments, solid phase reverse immobilization (SPRI) paramagnetic beads may be employed to separate the adapter-target-adapter polynucleotides from the unattached adapters. While such processes may enhance the purity of the resulting adapter-target-adapter polynucleotides, some unattached adapter oligonucleotides likely remain.

As used herein, "attached" or "bound" are used interchangeably in the context of an adapter relative to a target sequence. As described above, any suitable process may be used to attach an adapter to a target polynucleotide. For example, the adapter may be attached to the target through ligation with a ligase; through a combination of ligation of a portion of an adapter and addition of further or remaining portions of the adapter through extension, such as PCR, with primers containing the further or remaining portions of the adapters; trough transposition to incorporate a portion of an adapter and addition of further or remaining portions of the adapter through extension, such as PCR, with primers containing the further or remaining portions of the adapters; or the like. Preferably, the attached adapter oligonucleotide is covalently bound to the target polynucleotide.

Amplification

The polynucleotide resulting from attaching the adapter or portion of the adapter to the double stranded target is then subjected to amplification with primers having 5' ends that are modified to prevent digestion by an enzyme having 5' exonuclease activity.

The 5' ends of the primers may be modified in any suitable manner to prevent digestion by an enzyme having 5' exonuclease activity. For purposes of the present disclosure, a modification that "prevents" digestion by an exonuclease inhibits the activity of the exonuclease relative to its action on an unmodified end. Preferably, a modification that prevents digestion exonuclease eliminates the ability of the exonuclease to digest the polynucleotide strand. In some embodiments, the 5' ends of the primers comprise a phosphorothioate bond. Preferably, bonds between the terminal three nucleotides of the 5' ends of the primers comprise phosphorothioate bonds. For purpose of the present disclosure, an end of a polynucleotide whose bonds between the terminal three nucleotides comprise phosphorothioate bonds may be referred to as an end comprising three phosphorothioate bonds. Phosphorothioate bonds may be introduced into a 5' end of a polynucleotide in any suitable manner, as is well known in the art. Oligonucleotides comprising terminal phosphorothioate bonds may be purchased from a number of commercial vendors including, for example, Integrated DNA Technologies and Sigma-Aldrich.

If the adapter attached to the target prior to amplification is only a portion of the adapter, the remainder of the adapter may be provided by the 5' ends of the primers.

In either case, a first primer oligonucleotide for amplification that has a modified 5' end is configured to hybridize with a portion of the adapter or adapter portion in proximity to a 3' end of a strand of the adapter or portion. A second primer oligonucleotide for amplification that has a modified 5' end is configured to hybridize with a complement of a portion of the adapter or adapter portion in proximity to a 3' end of a strand of the complement of the adapter or portion. A complement of the adapter may result from extension of the first primer using the adapter-target-adapter as a template. Once the complement is formed, the second adapter may hybridize to the complement.

The first and second primers may be incubated with the polynucleotide resulting from attaching the adapter or portion of the adapter to the double stranded target (an "adapter-target-adapter" polynucleotide) under conditions suitable to amplify the adapter-target-adapter polynucleotides to produce polynucleotides having an amplified adapter-target-amplified adapter sequence with modified 5' ends. If the adapter-target-adapter polynucleotides comprise the entire adapter, the adapter-target-adapter polynucleotides may have the same sequence as the amplified adapter-target-amplified adapter sequence. If the adapter-target-adapter polynucleotides contain only a portion of the adapter, the amplified adapter-target-amplified adapter sequence will have additional nucleotides at the single stranded ends of the amplified adapter sequence due to the addition of the remainder of the adapter sequence from the primers.

As used herein, "conditions suitable for amplification" and its derivatives, generally refers to conditions suitable for amplifying one or more polynucleotide sequences. Such amplification may be linear or exponential. In some embodiments, the amplification conditions may include isothermal conditions or alternatively may include thermocycling conditions, or a combination of isothermal and thermocycling conditions. In some embodiments, the conditions suitable for amplifying one or more polynucleotide sequences include polymerase chain reaction (PCR) conditions. Typically, the amplification conditions refer to a reaction mixture that is sufficient to amplify polynucleotides such as one or more target sequences, or to amplify an amplified target sequence ligated to one or more adapters, e.g., an adapter-ligated amplified target sequence. Generally, the amplification conditions include a catalyst for amplification or for polynucleotide synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions may require hybridization or annealing of a primer to a nucleic acid, extension of the primer and a denaturing step in which the extended primer is separated from the polynucleotide sequence undergoing amplification. Typically, but not necessarily, amplification conditions may include thermocycling; in some embodiments, amplification conditions include a plurality of cycles where the steps of annealing, extending and separating are repeated. Typically, the amplification conditions include cations such as Mg++ or Mn++ and may also include various modifiers of ionic strength.

As used herein, the term "polymerase chain reaction" ("PCR") refers to the method of K. B. Mullis U.S. Pat. Nos. 4,683,195 and 4,683,202, which describe a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a series of thermal cycling in the presence of a DNA polymerase. The two primers are complementary to their respective strands of the double stranded polynucleotide of interest. The mixture is denatured at a higher temperature first and the primers are then annealed to complementary sequences within the polynucleotide of interest molecule. Following annealing, the primers are extended with a polymerase to form a new pair of complementary strands. The steps of denaturation, primer annealing and polymerase extension may be repeated many times (referred to as thermocycling) to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". In a modification to the method discussed above, the polynucleotides may be PCR amplified using a plurality of different primer pairs, in some cases, one or more primer pairs per polynucleotide of interest, thereby forming a multiplex PCR reaction.

Amplification of the adapter-target-adapter polynucleotides with the 5' modified primers results in a polynucleotide having amplified adapter-target-amplified adapter sequences with modified 5' ends.

The resulting amplified adapter includes a library-specific index tag sequence. Accordingly, the index tag is not itself formed by part of the target polynucleotide, but becomes part of the template for amplification on a solid surface for sequencing.

Preferably, the index tag sequence is 20 nucleotides or less in length. For example, the index tag sequence may be 1-10 nucleotides or 4-6 nucleotides in length. A four nucleotide index tag gives a possibility of multiplexing 256 samples on the same array, a six base index tag enables 4096 samples to be processed on the same array.

The amplified adapters may contain more than one index tag so that the multiplexing possibilities may be increased.

The library-specific index tag sequence may be located in a single-stranded, double-stranded region, or span the single-stranded and double-stranded regions of the adapter. Preferably, the index tag sequence is in a single-stranded region of the adapter.

The library-specific index tag sequence may be included on one or both of the 5' modified primers or may be included in a portion of the adapter that attached to the template fragment. If the library-specific index tag sequence is not included in the primers but is included in the portion of the adapter that is attached to the template fragment (and the primers add the remaining portion of the adapter), adapter-target-adapter polynucleotides from different libraries may be pooled to perform the amplification to the amplified adapter-target-amplified adapter polynucleotides. If the primers include the library-specific index tag sequence, then each library should be amplified separately prior to pooling.

In any case, the amplified adapters may include any other suitable sequence in addition to the index tag sequence. For example, the amplified adapters may comprise universal extension primer sequences, which are typically located at the 5' or 3' end of the amplified adapter and the resulting template polynucleotide for sequencing. The universal extension primer sequences may hybridize to complementary primers bound to a surface of a solid substrate. The complementary primers comprise a free 3' end from which a polymerase or other suitable enzyme may add nucleotides to extend the sequence using the hybridized library polynucleotide as a template, resulting in a reverse strand of the library polynucleotide being coupled to the solid surface. Such extension may be part of a sequencing run or cluster amplification.

In some embodiments, the amplified adapters comprise one or more universal sequencing primer sequences. The universal sequencing primer sequences may bind to sequencing primers to allow sequencing of an index tag sequence, a target sequence, or an index tag sequence and a target sequence.

The precise nucleotide sequence of the amplified adapters is generally not material to the invention and may be selected by the user such that the desired sequence elements are ultimately included in the common sequences of the library of templates derived from the amplified adaptors to, for example, provide binding sites for particular sets of universal extension primers and/or sequencing primers.

It will be understood that an "adapter-target-adapter sequence" or its equivalents refers to the orientation of the adapters relative to one another and to the target and does not necessarily mean that the sequence may not include additional sequences, such as linker sequences, for example.

Other libraries may be prepared in a similar manner, each including at least one library-specific index tag sequence or combinations of index tag sequences different than an index tag sequence or combination of index tag sequences from the other libraries.

A clean-up process, such as described above, may be performed on the resulting template polynucleotides having the amplified adapter-template-amplified adapter sequences.

The resulting adapter-target-adapter polynucleotides, whether or not first subjected to cleaned-up, along with any unincorporated primer oligonucleotides or remaining polynucleotides species are subjected to 3' blocking.

3' Blocking

3' blocking may be performed on each library separately or on pooled libraries. Preferably, 3' blocking is performed on pooled libraries.

3' blocked means that polynucleotides are modified to prevent incorporation of nucleotides on the 3' end to extend the polynucleotide from the 3' end or to prevent digestion by an enzyme having 3' exonuclease activity. Preferably, the 3' ends are blocked to prevent incorporation of nucleotides on the 3' end to extend the polynucleotide from the 3' end. More preferably, the 3' ends are blocked to prevent incorporation of nucleotides on the 3' end to extend the polynucleotide from the 3' end and to prevent digestion by an enzyme having 3' exonuclease activity.

In some embodiments, the 3'-OH blocking group may be removable, such that the 3' carbon atom has attached a group of the structure —O—Z, wherein Z is any of —C(R')$_2$—O—R", —C(R')$_2$—N(R")$_2$, —C(R')$_2$—N(H)R", —C(R')$_2$—S—R" and —C(R')$_2$—F, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; or (R')$_2$ represents an alkylidene group of formula=C(R''')$_2$ wherein each R''' may be the same or different and is selected from the group comprising hydrogen and halogen atoms and alkyl groups; and wherein said molecule may be reacted to yield an intermediate in which each R" is exchanged for H or, where Z is —C(R')$_2$—F, the F is exchanged for OH, SH or NH$_2$, preferably OH, which intermediate dissociates under aqueous conditions to afford a molecule with a free 3'OH; with the proviso that where Z is —C(R')$_2$—S—R", both R' groups are not H. Where the blocking group is any of —C(R')$_2$—O—R", —C(R')$_2$—N(R")$_2$, —C(R')$_2$—N(H)R", —C(R')$_2$—S—R" and —C(R')$_2$—F, i.e. of formula Z, each R' may be independently H or an alkyl. Preferably, Z is of formula —C(R')$_2$—O—R", —C(R')$_2$—N(R")$_2$, —C(R")$_2$—N(H)R" and —C(R')$_2$—SR". Particularly preferably, Z is of the formula —C(R')$_2$—O—R", —C(R')$_2$—N(R")$_2$, and —C(R')$_2$—SR". R" may be a benzyl group or a substituted benzyl group. One example of groups of structure —O—Z wherein Z is —C(R')$_2$—N(R")$_2$ are those in which —N(R")$_2$ is azido (—N$_3$). One such example is azidomethyl wherein each R' is H. Alternatively, R' in Z groups of formula —C(R')$_2$—N$_3$ and other Z groups may be any of the other groups discussed herein. Examples of typical R' groups include C$_{1-6}$ alkyl, particularly methyl and ethyl. Other non-limiting examples of suitable 3' blocking groups are provided in Greene et al., "Protective Groups in Organic Synthesis," John Wiley & Sons, New York (1991), U.S. Pat. Nos. 5,990,300, 5,872,244, 6,232,465, 6,214,987, 5,808,045, 5,763,594, 7,057,026, 7,566,537, 7,785,796, 8,148,064, 8,394,586, 9,388,463, 9,410,200, 7,427,673, 7,772,384, 8,158,346, 9,121,062, 7,541,444, 7,771,973, 8,071,739, 8,597,881, 9,121,060, 9,388,464, 8,399,188, 8,808,988, 9,051,612, 9,469,873, and U.S. Pub. Nos. 2016/0002721 and 2016/0060692, the entire contents of which are incorporated herein by reference.

3' blocking may be accomplished in any suitable manner. For example, a blocking moiety may be covalently attached to a 3' hydroxyl group at the 3' end to prevent extension from the 3' end. Preferably, the blocking group remains covalently bound during subsequent processes associated with immobilizing adapter-target-adapter polynucleotides to a solid surface and sequencing.

In some embodiments, a dideoxynucleotide (ddNTP) is incorporated onto the 3' end of a polynucleotide to block the 3' end. The ddNTP may be incorporated in any suitable manner. In some embodiments, a ddNTP is incorporated via a terminal deoxynucleotidyl transferase (TdT). TdTs are able to incorporated nucleotides onto a 3' end of single or double stranded DNA without a template. In some embodiments, a ddNTP is incorporated onto a 3' end via a TdT in the presence of a DNA polymerase, such as, for example, Pol19, Pol812 or Pol963 polymerase. Non-limiting examples of other suitable polymerases are provided in U.S. Pat. Nos. 8,460,910, 8,852,910, 8,623,628, 9,273,352, 9,447,389, and U.S. Pub. Nos. 2015/0376582, 2016/0032377, 2016/0090579, 2016/0115461, the entire contents of which are incorporated herein by reference.

In some embodiments, a digoxigenin-labeled dideoxyuridine triphosphate is added to the 3' end using terminal transferase to block the 3' end. Kits for adding digoxigenin-labeled dideoxyuridine triphosphate to a 3' end of a polynucleotide are available from, for example, Sigma-Aldrich.

Any other suitable process may also be employed to modify the 3' ends of the polynucleotides.

During or following 3' blocking a number of compounds and compositions may result. For example, a polynucleotide may result that has a first adapter-target-second adapter sequence of nucleotides in which a 5' ends of the polynucleotides are blocked and the 3' ends of the polynucleotide is blocked. Compositions or libraries comprising the 5' modified and 3' blocked polynucleotides may result. Pooled libraries and composition comprising pooled libraries of such polynucleotides may result.

By way of further example, a composition comprising such polynucleotides and an enzyme and reagent for blocking 3' ends of the polynucleotide may result. Similarly, a composition comprising a library of polynucleotides and the enzyme and reagent may result. Compositions comprising pooled libraries of such polynucleotides and the enzyme and reagent may result. In some embodiments, the compositions comprise a ddNTP. The compositions may further comprise a TdT. The compositions may further comprise a DNA polymerase, such as, for example, Pol19, Pol812 or Pol963 polymerase.

A clean-up process, such as described above, may be performed following blocking.

Exonuclease Treatment

After (or during) blocking the resulting solutions or compositions comprising the resulting polynucleotides, whether or not first subjected to cleanup may, optionally, be subjected to treatment with an exonuclease. Preferably, the exonuclease treatment has 3' exonuclease activity to degrade any polynucleotides that remain that are not 3' blocked. Because the 5' ends are exonuclease resistant, the exonuclease may have both 5' exonuclease activity and 3' exonuclease activity.

An exonuclease that has "5' exonuclease activity" is an exonuclease that digests DNA in a 5' to 3' direction. An exonuclease that has "3' exonuclease activity" is an exonuclease that digests DNA in a 3' to 5' direction.

One example of a suitable exonuclease that has both 5' and 3' exonuclease activity is Exonuclease V, which is a RecBCD complex from *E. coli* and is available from, for example, New England Biolabs. Exonuclease V also has activity for double-stranded DNA without nicking.

Exonuclease treatment may be performed on each library separately or on pooled libraries. Following exonuclease treatment, a clean-up step, such as described above, may be performed prior to immobilizing the polynucleotides on a solid surface for sequencing.

If the libraries have not been pooled, they may be pooled prior to immobilizing on a surface of sequencing.

Preparation of Immobilized Samples for Sequencing

The pooled 5' modified and 3' blocked library preparations may then be immobilized on a solid surface for in preparation for sequencing. Sequencing may be performed as an array of single molecules, or may be amplified prior to sequencing. The amplification may be carried out using one or more immobilized primers. The immobilized primer(s) may be a lawn on a planar surface, clusters on a planar surface, in wells of a multi-well structure, on a pool of beads, or the like. The pool of beads may be isolated into an emulsion with a single bead in each "compartment" of the emulsion. At a concentration of only one template per "compartment", only a single template is amplified on each bead.

The term "solid-phase amplification" as used herein refers to any polynucleotide amplification reaction carried out on or in association with a solid support such that all or a portion of the amplified products are immobilized on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers is/are immobilized on the solid support. Solid phase PCR covers systems such as emulsions, wherein one primer is anchored to a bead and the other is in free solution, and colony formation in solid phase gel matrices wherein one primer is anchored to the surface, and one is in free solution.

Although the disclosure encompasses "solid-phase" amplification methods in which only one amplification primer is immobilized (the other primer usually being present in free solution), it is preferred for the solid support to be provided with both the forward and the reverse primers immobilized. In practice, there will be a "plurality" of identical forward primers and/or a "plurality" of identical reverse primers immobilized on the solid support, since the amplification process requires an excess of primers to sustain amplification. References herein to forward and reverse primers are to be interpreted accordingly as encompassing a "plurality" of such primers unless the context indicates otherwise.

As will be appreciated by the skilled reader, any given amplification reaction requires at least one type of forward primer and at least one type of reverse primer specific for the template to be amplified. However, in certain embodiments the forward and reverse primers may comprise template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the invention. Other embodiments may use forward and reverse primers which contain identical template-specific sequences but which differ in some other structural features. For example one type of primer may contain a non-nucleotide modification which is not present in the other.

Throughout this disclosure, the terms "P5" and "P7" are used when referring to adapters and/or amplification primers. It will be understood that any suitable amplification primers can be used in the methods presented herein, and that the use of P5 and P7 are exemplary embodiments only. Uses of amplification primers such as P5 and P7 on flowcells is known in the art, as exemplified by the disclosures of WO 2007/010251, WO 2006/064199, WO 2005/065814, WO 2015/106941, WO 1998/044151, and WO 2000/018957, each of which is incorporated by reference in its entirety. For example, any suitable forward amplification primer, whether immobilized or in solution, can be useful in the methods presented herein for hybridization to a complementary sequence and amplification of a sequence. Similarly, any suitable reverse amplification primer, whether immobilized or in solution, can be useful in the methods presented herein for hybridization to a complementary sequence and amplification of a sequence. One of skill in the art will understand how to design and use primer sequences that are suitable for capture, and amplification of nucleic acids as presented herein.

Primers for solid-phase amplification are preferably immobilized by single point covalent attachment to the solid support at or near the 5' end of the primer, leaving the template-specific portion of the primer free to anneal to its cognate template and the 3' hydroxyl group free for primer extension. Any suitable covalent attachment means known in the art may be used for this purpose. The chosen attachment chemistry will depend on the nature of the solid support, and any derivatization or functionalization applied to it. The primer itself may include a moiety, which may be a non-nucleotide chemical modification, to facilitate attachment. In some embodiments, the primer includes include a sulfur-containing nucleophile, such as phosphorothioate or thiophosphate, at the 5' end. The surface of the solid support may include or be modified to include a moiety to which the sulfur-containing nucleophile may attach. For example, a sulfur-containing nucleophile may bind to a bromoacetamide group. In some embodiments a solid-supported polyacrylamide hydrogel comprises a bromoacetamide group for binding a sulfur-containing nucleophile. A more particular means of attaching primers and templates to a solid support is via 5' phosphorothioate attachment to a hydrogel comprised of polymerized acrylamide and N-(5-bromoacetamidylpentyl) acrylamide (BRAPA), as described fully in WO 2005/065814.

Solid supports comprised of an inert substrate or matrix (e.g. glass slides, polymer beads, etc) may be "functionalized", for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel), but the intermediate material may itself be non-covalently attached to the substrate or matrix (e.g. the glass substrate). The term "covalent attachment to a solid support" is to be interpreted accordingly as encompassing this type of arrangement.

The pooled library samples may be amplified on a solid surface contains a forward and reverse amplification primer. In some embodiments, the pooled libraries of polynucleotides are used to prepare clustered arrays of polynucleic acid colonies, analogous to those described in U.S. Pat. Pub. No. 2005/0100900, U.S. Pat. No. 7,115,400, WO 00/18957 and WO 98/44151, by solid-phase amplification and more particularly solid phase isothermal amplification. The terms "cluster" and "colony" are used interchangeably herein to refer to a discrete site on a solid support comprised of a plurality of identical immobilized nucleic acid strands and a plurality of identical immobilized complementary nucleic acid strands. The term "clustered array" refers to an array formed from such clusters or colonies. In this context the term "array" is not to be understood as requiring an ordered arrangement of clusters.

The term solid phase, or surface, is used to mean either a planar array wherein primers are attached to a flat surface, for example, glass, silica or plastic microscope slides or similar flow cell devices; beads, wherein either one or two primers are attached to the beads and the beads are amplified; an array of beads on a surface after the beads have been amplified; or the like.

The terms "solid surface," "solid support" and other grammatical equivalents herein refer to any material that is appropriate for or may be modified to be appropriate for the attachment of the template polynucleotides. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon®, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. Particularly useful solid supports and solid surfaces for some embodiments are located within a flow cell apparatus. Exemplary flow cells are set forth in further detail below.

In some embodiments, the solid support comprises a patterned surface. A "patterned surface" refers to an arrangement of different regions in or on an exposed layer of a solid support. For example, one or more of the regions may be features where one or more amplification primers are present. The features may be separated by interstitial regions where amplification primers are not present. In some embodiments, the pattern may be an x-y format of features that are in rows and columns. In some embodiments, the pattern may be a repeating arrangement of features and/or interstitial regions. In some embodiments, the pattern may be a random arrangement of features and/or interstitial regions. Exemplary patterned surfaces that may be used in the methods and compositions set forth herein are described in U.S. Pat. Nos. 8,778,848, 8,778,849, 9,079,148, and U.S. Pub. No. 2014/0243224.

In some embodiments, the solid support comprises an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface may be wells in an array of wells (e.g. microwells or nanowells) on glass, silicon, plastic or other suitable solid supports with patterned, covalently-linked gel such as poly(N-(5-azidoacetamidylpentyl)acrylamide-co-acrylamide) (PAZAM, see, for example, U.S. Pub. No. 2013/184796, WO 2016/066586, and WO 2015/002813). The process creates gel pads used for sequencing that may be stable over sequencing runs with a large number of cycles. The covalent linking of the polymer to the wells is helpful for maintaining the gel in the structured features throughout the lifetime of the structured substrate during a variety of uses. However in many embodiments, the gel need not be covalently linked to the wells. For example, in some conditions silane free acrylamide (SFA, see, for example, U.S. Pat. No. 8,563,477) which is not covalently attached to any part of the structured substrate, may be used as the gel material.

In particular embodiments, a structured substrate may be made by patterning a solid support material with wells (e.g. microwells or nanowells), coating the patterned support with a gel material (e.g. PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids may be attached to gel material. A solution of target nucleic acids (e.g. a fragmented human genome) may then be contacted with the polished substrate such that individual target nucleic acids will seed individual wells via interactions with primers attached to the gel material; however, the target nucleic acids will not occupy the interstitial regions due to absence or inactivity of the gel material. Amplification of the target nucleic acids will be confined to the wells since absence or inactivity of gel in the interstitial regions prevents outward migration of the growing nucleic acid colony. The process is conveniently manufacturable, being scalable and utilizing conventional micro- or nanofabrication methods.

The term "flowcell" as used herein refers to a chamber comprising a solid surface across which one or more fluid reagents may be flowed. Examples of flowcells and related fluidic systems and detection platforms that may be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082.

In some embodiments, the solid support or its surface is non-planar, such as the inner or outer surface of a tube or vessel. In some embodiments, the solid support comprises microspheres or beads. By "microspheres" or "beads" or "particles" or grammatical equivalents herein is meant small discrete particles. Suitable bead compositions include, but are not limited to, plastics, ceramics, glass, polystyrene, methylstyrene, acrylic polymers, paramagnetic materials, thoria sol, carbon graphite, titanium dioxide, latex or crosslinked dextrans such as Sepharose, cellulose, nylon, crosslinked micelles and Teflon®, as well as any other materials outlined herein for solid supports may all be used. "Microsphere Detection Guide" from Bangs Laboratories, Fishers Ind. is a helpful guide. In certain embodiments, the microspheres are magnetic microspheres or beads.

The beads need not be spherical; irregular particles may be used. Alternatively or additionally, the beads may be porous. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller or larger beads may be used.

Clustered arrays may be prepared using either a process of thermocycling, as described in WO/9844151, or a process whereby the temperature is maintained as a constant, and the cycles of extension and denaturing are performed using changes of reagents. Such isothermal amplification methods are described in patent application numbers WO/0246456 and US 2008/0009420. Due to the lower temperatures required in the isothermal process, this is particularly preferred.

It will be appreciated that any of the amplification methodologies described herein or generally known in the art may be utilized with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354, which is incorporated herein by reference in its entirety. The above amplification methods may be employed to amplify one or more nucleic acids of interest. For example, PCR, including multiplex PCR, SDA, TMA, NASBA and the like may be utilized to amplify immobilized DNA fragments. In some embodiments, primers directed specifically to the polynucleotide of interest are included in the amplification reaction.

Other suitable methods for amplification of polynucleotides may include oligonucleotide extension and ligation, rolling circle amplification (RCA) (Lizardi et al., Nat. Genet. 19:225-232 (1998)) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835) technologies. It will be appreciated that these amplification methodologies may be designed to amplify immobilized DNA fragments. For example, in some embodiments, the amplification method may include ligation probe amplification or oligonucleotide ligation assay (OLA) reactions that contain primers directed specifically to the nucleic acid of interest. In some embodiments, the amplification method may include a primer extension-ligation reaction that contains primers directed specifically to the nucleic acid of interest. As a non-limiting example of primer extension and ligation primers that may be specifically designed to amplify a nucleic acid of interest, the amplification may include primers used for the GoldenGate assay (Illumina, Inc., San Diego, CA) as exemplified by U.S. Pat. Nos. 7,582,420 and 7,611,869.

Exemplary isothermal amplification methods that may be used in a method of the present disclosure include, but are not limited to, Multiple Displacement Amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587. Other non-PCR-based methods that may be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyper-branched strand displacement amplification which is described in, for example Lage et al., Genome Res. 13:294-307 (2003). Isothermal amplification methods may be used with the strand-displacing Phi 29 polymerase or Bst DNA polymerase large fragment, 5'->3' exo- for random primer amplification of genomic DNA. The use of these polymerases takes advantage of their high processivity and strand displacing activity. High processivity allows the polymerases to produce fragments that are 10-20 kb in length. As set forth above, smaller fragments may be produced under isothermal conditions using polymerases having low processivity and strand-displacing activity such as Klenow polymerase. Additional description of amplification reactions, conditions and components are set forth in detail in the disclosure of U.S. Pat. No. 7,670,810, which is incorporated herein by reference in its entirety.

Another polynucleotide amplification method that is useful in the present disclosure is Tagged PCR which uses a population of two-domain primers having a constant 5' region followed by a random 3' region as described, for example, in Grothues et al. *Nucleic Acids Res.* 21(5):1321-2 (1993). The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers may be removed and further replication may take place using primers complementary to the constant 5' region.

In some embodiments, isothermal amplification can be performed using kinetic exclusion amplification (KEA), also referred to as exclusion amplification (ExAmp). A nucleic acid library of the present disclosure can be made using a method that includes a step of reacting an amplification reagent to produce a plurality of amplification sites that each includes a substantially clonal population of amplicons from an individual target nucleic acid that has seeded the site. In some embodiments the amplification reaction proceeds until a sufficient number of amplicons are generated to fill the capacity of the respective amplification site. Filling an already seeded site to capacity in this way inhibits target nucleic acids from landing and amplifying at the site thereby producing a clonal population of amplicons at the site. In some embodiments, apparent clonality can be achieved even if an amplification site is not filled to capacity prior to a second target nucleic acid arriving at the site. Under some conditions, amplification of a first target nucleic acid can proceed to a point that a sufficient number of copies are made to effectively outcompete or overwhelm production of copies from a second target nucleic acid that is transported to the site. For example in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

As demonstrated by the above example, amplification sites in an array can be, but need not be, entirely clonal in particular embodiments. Rather, for some applications, an individual amplification site can be predominantly populated with amplicons from a first target nucleic acid and can also have a low level of contaminating amplicons from a second target nucleic acid. An array can have one or more amplification sites that have a low level of contaminating amplicons so long as the level of contamination does not have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual amplification site for particular applications include, but are not limited to, at most 0.1%, 0.5%, 1%, 5%, 10% or 25% contaminating amplicons. An array can include one or more amplification sites having these exemplary levels of contaminating amplicons. For example, up to 5%, 10%, 25%, 50%, 75%, or even 100% of the amplification sites in an array can have some contaminating amplicons. It will be understood that in an array or other collection of sites, at least 50%, 75%, 80%, 85%, 90%, 95% or 99% or more of the sites can be clonal or apparently clonal.

In some embodiments, kinetic exclusion can occur when a process occurs at a sufficiently rapid rate to effectively exclude another event or process from occurring. Take for example the making of a nucleic acid array where sites of the array are randomly seeded with target nucleic acids from a solution and copies of the target nucleic acid are generated in an amplification process to fill each of the seeded sites to capacity. In accordance with the kinetic exclusion methods of the present disclosure, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Kinetic exclusion amplification methods can be performed as described in detail in the disclosure of U.S. Pub. No. 2013/0338042, which is incorporated herein by reference in its entirety.

Kinetic exclusion can exploit a relatively slow rate for initiating amplification (e.g. a slow rate of making a first copy of a target nucleic acid) vs. a relatively rapid rate for making subsequent copies of the target nucleic acid (or of the first copy of the target nucleic acid). In the example of the previous paragraph, kinetic exclusion occurs due to the relatively slow rate of target nucleic acid seeding (e.g. relatively slow diffusion or transport) vs. the relatively rapid rate at which amplification occurs to fill the site with copies of the nucleic acid seed. In another exemplary embodiment, kinetic exclusion can occur due to a delay in the formation of a first copy of a target nucleic acid that has seeded a site (e.g. delayed or slow activation) vs. the relatively rapid rate at which subsequent copies are made to fill the site. In this example, an individual site may have been seeded with several different target nucleic acids (e.g. several target nucleic acids can be present at each site prior to amplification). However, first copy formation for any given target nucleic acid can be activated randomly such that the average rate of first copy formation is relatively slow compared to the rate at which subsequent copies are generated. In this case, although an individual site may have been seeded with several different target nucleic acids, kinetic exclusion will allow only one of those target nucleic acids to be amplified. More specifically, once a first target nucleic acid has been activated for amplification, the site will rapidly fill to capacity with its copies, thereby preventing copies of a second target nucleic acid from being made at the site.

An amplification reagent can include further components that facilitate amplicon formation and, in some cases, increase the rate of amplicon formation. An example is a recombinase. Recombinase can facilitate amplicon formation by allowing repeated invasion/extension. More specifically, recombinase can facilitate invasion of a target nucleic acid by the polymerase and extension of a primer by the polymerase using the target nucleic acid as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590, the contents of which are incorporated herein by reference.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g. via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, MA). Further, examples of useful formulations that include a helicase protein are described in U.S. Pat. Nos. 7,399,590 and 7,829,284, each of which is incorporated herein by reference.

Yet another example of a component that can be included in an amplification reagent to facilitate amplicon formation and in some cases increase the rate of amplicon formation is an origin binding protein.

Use in Sequencing/Methods of Sequencing

The immobilized polynucleotides from the pooled libraries may be sequenced in any suitable manner. Preferably, sequencing is performed by sequencing by synthesis in which nucleotides are added successively to a free 3' hydroxyl group of a sequencing primer using the immobilized polynucleotides as a template, resulting in synthesis of a polynucleotide chain in the 5' to 3' direction. The nature of the nucleotide added is preferably determined after each nucleotide addition. Sequencing techniques using sequencing by ligation, wherein not every contiguous base is sequenced, and techniques such as massively parallel signature sequencing (MPSS) where bases are removed from, rather than added to the strands on the surface are also within the scope of the disclosure, as are techniques using detection of pyrophosphate release (pyrosequencing). Such pyrosequencing based techniques are particularly applicable to sequencing arrays of beads where the beads have been amplified in an emulsion such that a single template from the library molecule is amplified on each bead.

The initiation point for the sequencing reaction may be provided by annealing of a sequencing primer to a product of the solid-phase amplification reaction. In this connection, one or both of the adapters added during formation of the template library may include a nucleotide sequence which permits annealing of a sequencing primer to immobilized polynucleotides, such as the adapter-target-adapter polynucleotides.

The index tag sequence and target sequence may be determined in a single read from a single sequencing primer, or in multiple reads from more than one sequencing primers. In the case of two reads from two sequencing primers, the "index tag read" and the "target read" may be performed in either order, with a suitable denaturing step to remove the annealed primer after the first sequencing read is completed. Suitable denaturing steps may include formamide, hydroxide or heat as generally known in the art.

The products of solid-phase amplification reactions where both forward and reverse amplification primers are covalently immobilized on the solid surface may be so-called "bridged" structures formed by annealing of pairs of immobilized polynucleotide strands and immobilized complementary strands, both strands being attached to the solid support at the 5' end. Arrays comprised of such bridged structures provide inefficient templates for nucleic acid sequencing, since hybridization of a conventional sequencing primer to one of the immobilized strands is not favored compared to annealing of this strand to its immobilized complementary strand under standard conditions for hybridization. Examples of bridged or cluster amplification are described in, for example, U.S. Pat. Nos. 7,985,565 and 7,115,400.

In order to provide more suitable templates for nucleic acid sequencing, it is preferred to remove substantially all or remove or displace at least a portion of one of the immobilized strands in the "bridged" structure to generate a template which is at least partially single-stranded. The portion of the template which is single-stranded will thus be available for hybridization to a sequencing primer. The process of removing all or a portion of one immobilized strand in a "bridged" double-stranded nucleic acid structure may be referred to herein as 'linearization', and is described in further detail in WO 2007/010251, WO 2006/064199, WO 2005/065814, WO 2015/106941, WO 1998/044151, and WO 2000/018957.

Bridged template structures may be linearized by cleavage of one or both strands with a restriction endonuclease or by cleavage of one strand with a nicking endonuclease. Other methods of cleavage may be used as an alternative to restriction enzymes or nicking enzymes, including inter alia chemical cleavage (e.g. cleavage of a diol linkage with periodate), cleavage of abasic sites by cleavage with endonuclease (for example 'USER', as supplied by NEB, Cat #M5505S), or by exposure to heat or alkali, cleavage of ribonucleotides incorporated into amplification products otherwise comprised of deoxyribonucleotides, photochemical cleavage or cleavage of a peptide linker.

It will be appreciated that a linearization step may not be essential if the solid-phase amplification reaction is performed with only one primer covalently immobilized and the other in free solution.

Following the cleavage step, regardless of the method used for cleavage, the product of the cleavage reaction may be subjected to denaturing conditions in order to remove the portion(s) of the cleaved strand(s) that are not attached to the solid support. Suitable denaturing conditions, for example sodium hydroxide solution, formamide solution or heat, will be apparent to the skilled reader with reference to standard molecular biology protocols (Sambrook et al., 2001, Molecular Cloning, A Laboratory Manual, 3rd Ed, Cold Spring Harbor Laboratory Press, Cold Spring Harbor Laboratory Press, NY; Current Protocols, eds. Ausubel et al.). Denaturation results in the production of a sequencing template which is partially or substantially single-stranded. A sequencing reaction may then be initiated by hybridization of a sequencing primer to the single-stranded portion of the template.

Thus, in some embodiments, a sequencing reaction comprises hybridizing a sequencing primer to a single-stranded region of a linearized amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand.

One preferred sequencing method which may be used relies on the use of modified nucleotides having removable 3' blocks, for example as described in WO 2004/018497 and U.S. Pat. No. 7,057,026. Once the modified nucleotide has been incorporated into the growing polynucleotide chain complementary to the region of the template being sequenced there is no free 3'—OH group available to direct further sequence extension and therefore the polymerase cannot add further nucleotides. Once the nature of the base incorporated into the growing chain has been determined, the 3' block may be removed to allow addition of the next successive nucleotide. By ordering the products derived using these modified nucleotides, it is possible to deduce the DNA sequence of the DNA template. Such reactions may be done in a single experiment if each of the modified nucleotides has a different label attached thereto, known to correspond to the particular base, to facilitate discrimination between the bases added during each incorporation step. Alternatively, a separate reaction may be carried out containing each of the modified nucleotides separately.

The modified nucleotides may carry a label to facilitate their detection. A fluorescent label, for example, may be used for detection of modified nucleotides. Each nucleotide type may thus carry a different fluorescent label, for example, as described in WO 2007/135368. The detectable label need not, however, be a fluorescent label. Any label may be used which allows the detection of an incorporated nucleotide.

One method for detecting fluorescently labelled nucleotides comprises using laser light of a wavelength specific for the labelled nucleotides, or the use of other suitable sources of illumination. The fluorescence from the label on the nucleotide may be detected by a CCD camera or other suitable detection means. Suitable instrumentation for recording images of clustered arrays is described in WO 2007/123744.

Of course, any other suitable sequencing method may be employed. Preferably, the sequencing method relies on successive incorporation of nucleotides into a polynucleotide chain. Suitable alternative techniques include, for example, pyrosequencing, FISSEQ (fluorescent in situ sequencing), MPSS and sequencing by ligation-based methods, for example as described is U.S. Pat. No. 6,306,597.

The nucleic acid sample may be further analyzed to obtain a second read from the opposite end of the fragment. Methodology for sequencing both ends of a cluster are described in WO 2007/010252 and WO 2008/041002. In one example, the series of steps may be performed as follows; generate clusters, linearize, hybridize first sequencing primer and obtain first sequencing read. The first sequencing primer may be removed, a second primer hybridized and the index tag sequenced. The poly nucleotide strand may then be "inverted" on the surface by synthesizing a complementary copy from the remaining immobilized primers used in cluster amplification. This process of strand resynthesize regenerates the double stranded cluster. The original template strand may be removed, to linearize the resynthesized strand that may then be annealed to a sequencing primer and sequenced in a third sequencing run.

In the cases where strand re-synthesis is employed, both strands may be immobilized to the surface in a way that allows subsequent release of a portion of the immobilized strand. This may be achieved through a number of mechanisms as described in WO 2007/010251. For example, one primer may contain a uracil nucleotide, which means that the strand may be cleaved at the uracil base using the enzymes uracil glycosylase (UDG) which removes the nucleoside base, and endonuclease VIII that excises the abasic nucleotide. This enzyme combination is available as USER™ enzyme from New England Biolabs (Cat #M5505). The second primer may comprise an 8-oxoguanine nucleotide, which is then cleavable by the enzyme FPG (NEB Cat #M0240). This design of primers provides control of which primer is cleaved at which point in the process, and also where in the cluster the cleavage occurs. The primers may also be chemically modified, for example with a disulfide or diol modification that allows chemical cleavage at specific locations.

Referring now to FIG. 1, a schematic drawing illustrating an embodiment of a process for producing 5' modified and 3' blocked template polynucleotides for immobilizing on a solid surface for sequencing is shown. In FIG. 1A, a double stranded target polynucleotide fragment is shown. Initial portions of adapters may be attached to the ends of the target by ligation (see FIG. 1B) or tagmentation. The portions of the adapters (ab) comprise a double stranded portion attached to the double stranded target and single stranded portions extending away from the target to the 5' and 3' ends. A 5' modified primer (B') is configured to hybridize to a single stranded portion of the adapter (b) in proximity to the 3' end (FIG. 1C). A polymerase may be used to extend the primer B' using the portions of the adapter and the target as a template to produce a complement of the portions of the adapter (a') and the target (FIG. 1D, strands from FIG. 1C removed for purposes of convenience and clarity). A 5' modified primer (A) is configured to hybridize to a single stranded portion of the complement of the adapter portion (a') in proximity to the 3' end (FIG. 1E). A polymerase may be used to extend the primer A using the portions of the complement of the adapters and target as a template to produce portions of the adapter (b) and the target (FIG. 1F, strands from FIG. 1E removed for purposes of convenience and clarity).

If the adapter portion that is added by, for example, ligation or tagmentation includes the library specific index tag sequence at a location between the sequence for hybridization of the primers (A, B') and the target (when the portion of the adapter is attached to the target), amplification (FIGS. 1C-F) with primers (A, B') may be performed on pooled target fragments from different libraries, provided that each fragment from each library includes a portion of an adapter having a library specific index tag sequence in a similar location and each portion of the adapter from each library has a sequence (or complement) to which primers (A, B') may hybridize. Otherwise, each library should be amplified separately.

The resulting 5' protected template (amplified adapter-target-amplified adapter) may be subjected to 3' blocking to produce a 5' and 3' protected template polynucleotide (FIG. 1G) for immobilizing on a solid surface for sequencing. 3' blocking may affect any polynucleotide present in solution with the 5' protected template, including any other amplification fragments or residual polynucleotides (not shown). Accordingly, if adaptor portions (ab) are amplified with primers (A, B), the amplified adapters that are not attached to the template (not shown) should also be 3' blocked.

Exonuclease treatment may optionally be applied to the resulting mixture. Remaining unblocked or unprotected polynucleotides may be degraded prior to immobilizing the template polynucleotides on a solid surface.

Figure 2:
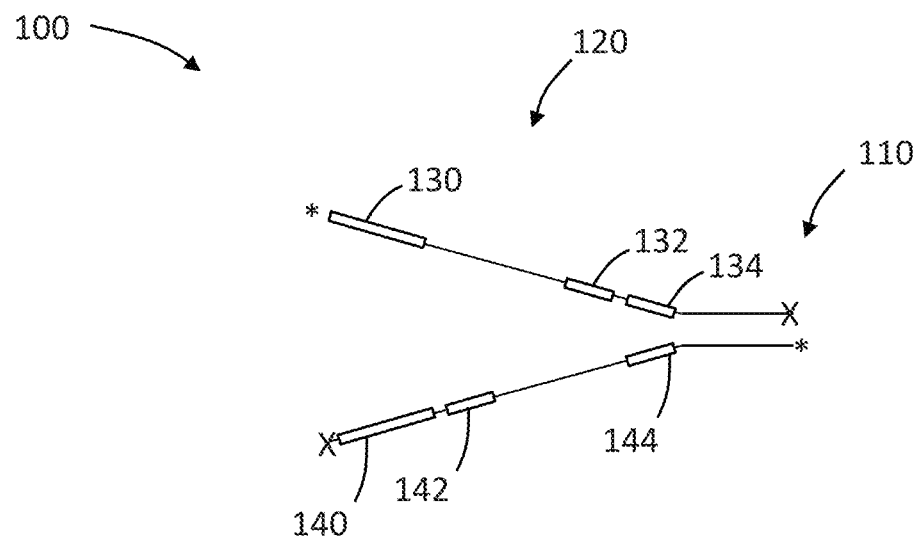
FIG. 2 is a schematic drawing of an embodiment of an adapter according to various aspects of the disclosure presented herein.

Referring now to FIG. 2 a schematic drawing is shown of an adapter (amplified adapter) 100 that may be used or result during amplification of the libraries in preparation for sequencing. The depicted adapter 100 comprises a double-stranded region 110 and a non-complementary single-stranded region 120. The 5' ends are modified (indicated by the "*") to prevent degradation by an exonuclease, and the 3' ends are blocked (indicated by the "X"). One depicted strand of the adapter 100 comprises a universal extension primer sequence 130, an index tag sequence 132, and a sequencing primer sequence 134. The other depicted strand of the adapter 100 comprises a universal extension primer sequence 140, an index tag sequence 142, and a sequencing primer sequence 144.

The universal extension primer sequences 130, 140 may hybridize to extension primer oligonucleotides attached to a solid surface for purposes of amplification or sequencing (if the adapter 100 were attached to a target polynucleotide). Universal extension primer sequence 140, or a portion thereof, may also hybridize to a sequencing primer for sequencing index tag sequence 142. Alternatively, the strand may comprise a further sequencing primer sequence (not shown).

Sequencing primer sequence 134 may hybridize to a sequencing primer to allow sequencing of index tag sequence 132. Index tag sequence 142 and index tag sequence 132 may be the same or different.

Sequencing primer sequence 144 may hybridize to a sequencing primer to allow sequencing of a target polynucleotide sequence (if attached to the adapter 100).

Sequencing primer sequences 134, 144 may hybridize to, for example, PCR primers if the adapters are attached to a target in a multi-step process as described above.

It will be understood that a suitable adapter for used in various embodiments described herein may have more or less sequence features, or other sequence features, than those described regarding FIG. 2.

Figure 3:
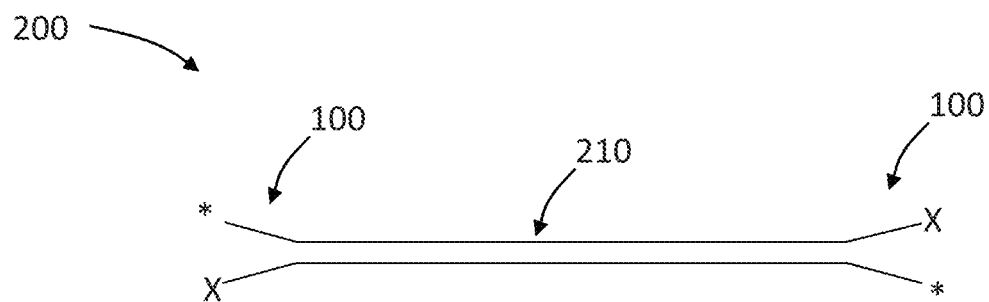
FIG. 3 is a schematic drawing of an embodiment of a template polynucleotide having an adapter-target-adapter sequence (which may include an adapter generally as shown in FIG. 2) according to various aspects of the disclosure presented herein.

Referring now to FIG. 3, a schematic drawing of a template polynucleotide 200 of a library having an adapter 100—template 210—adapter 100 sequence is shown. The template polynucleotide 210 is double stranded and attached to a double stranded portion of the first 100 and second 101 adapters. The 3' ends of the template polynucleotide 200 are blocked and the 5' ends are modified, e.g., as described above.

Figure 4:
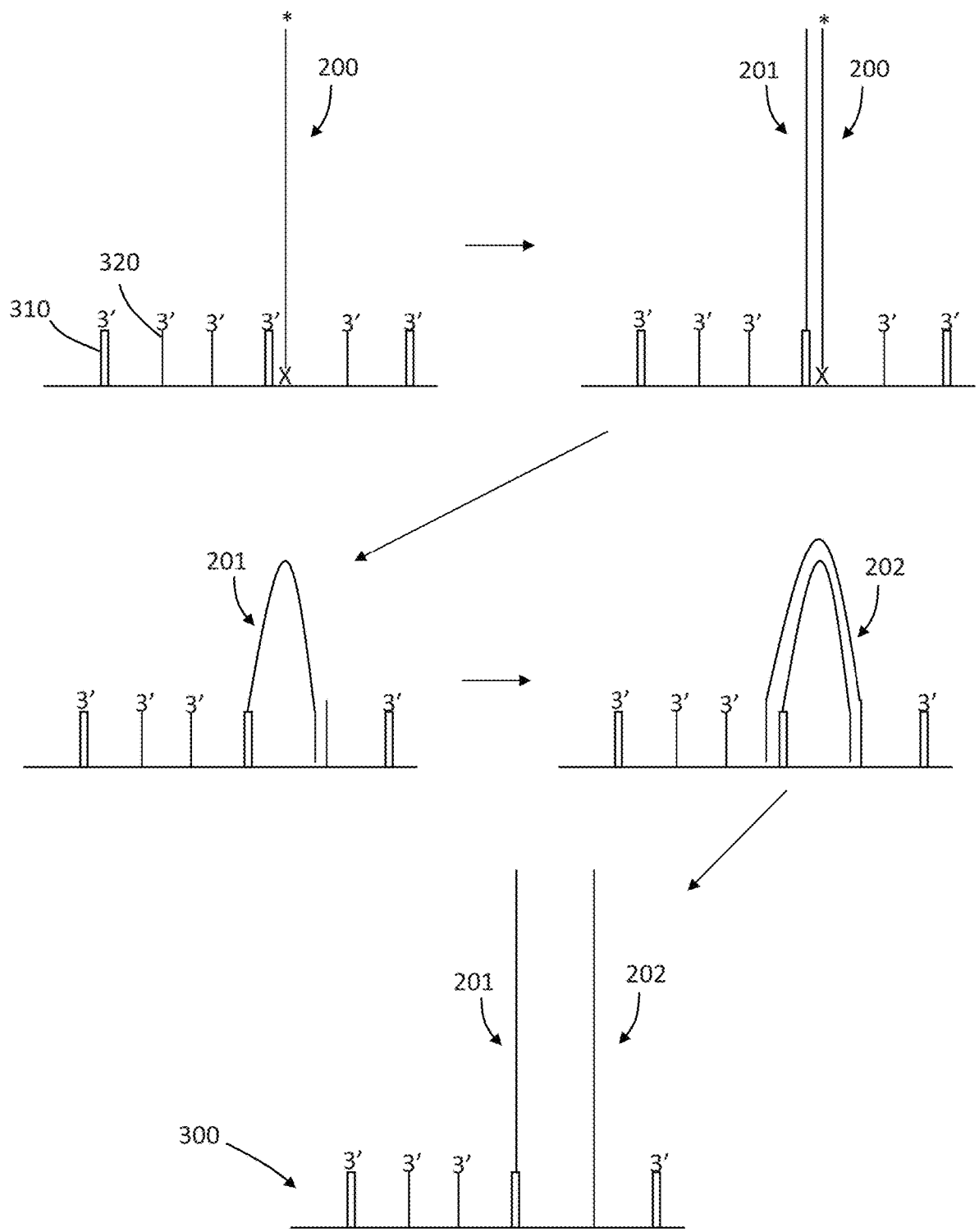
FIG. 4 is a schematic drawing illustrating an embodiment of a process for cluster amplification employing an embodiment of a template polynucleotide (which may be the template polynucleotide depicted in FIG. 3) according to various aspects of the disclosure presented herein.

Referring now to FIG. 4, a schematic illustration of a process for cluster amplification of a template polynucleotide 200 from a library to a solid surface 300 to prepare for sequencing is shown. In the first panel, the template polynucleotide 200 having a modified 5' end and a blocked 3' end is hybridized to a first extension primer 310 attached to the solid surface 300. For example, universal extension primer sequence 140 depicted in FIG. 2 of the adapter portion may hybridize to the first extension primer 310.

The first extension primer 310 comprises a free 3' end, and thus nucleotides may be added to the 3' end using the template polynucleotide 200 as a template to produce a copy template strand 201 (see second panel) attached to the solid surface 300 in the presence of a suitable polymerase. The template strand 200 may be removed and the copy strand 201 may hybridize with a second extension primer 320 attached to the solid surface 300 (see third panel). For example, universal extension primer sequence 130 depicted in FIG. 2 of the adapter portion may hybridize to the second extension primer 320.

The second extension primer 320 comprises a free 3' end, and thus nucleotides may be added to the 3' end using the copy template polynucleotide 201 as a template to produce an amplified template strand 202 (see fourth panel) attached to the solid surface 300 in the presence of a suitable polymerase. Additional rounds of amplification may be performed to produce a cluster of copy template strands 201 and amplified template strands 202.

For purposes of illustration, the fifth panel of FIG. 4 depicts the copy 201 and amplified 202 template strands in linear form.

Figure 5:
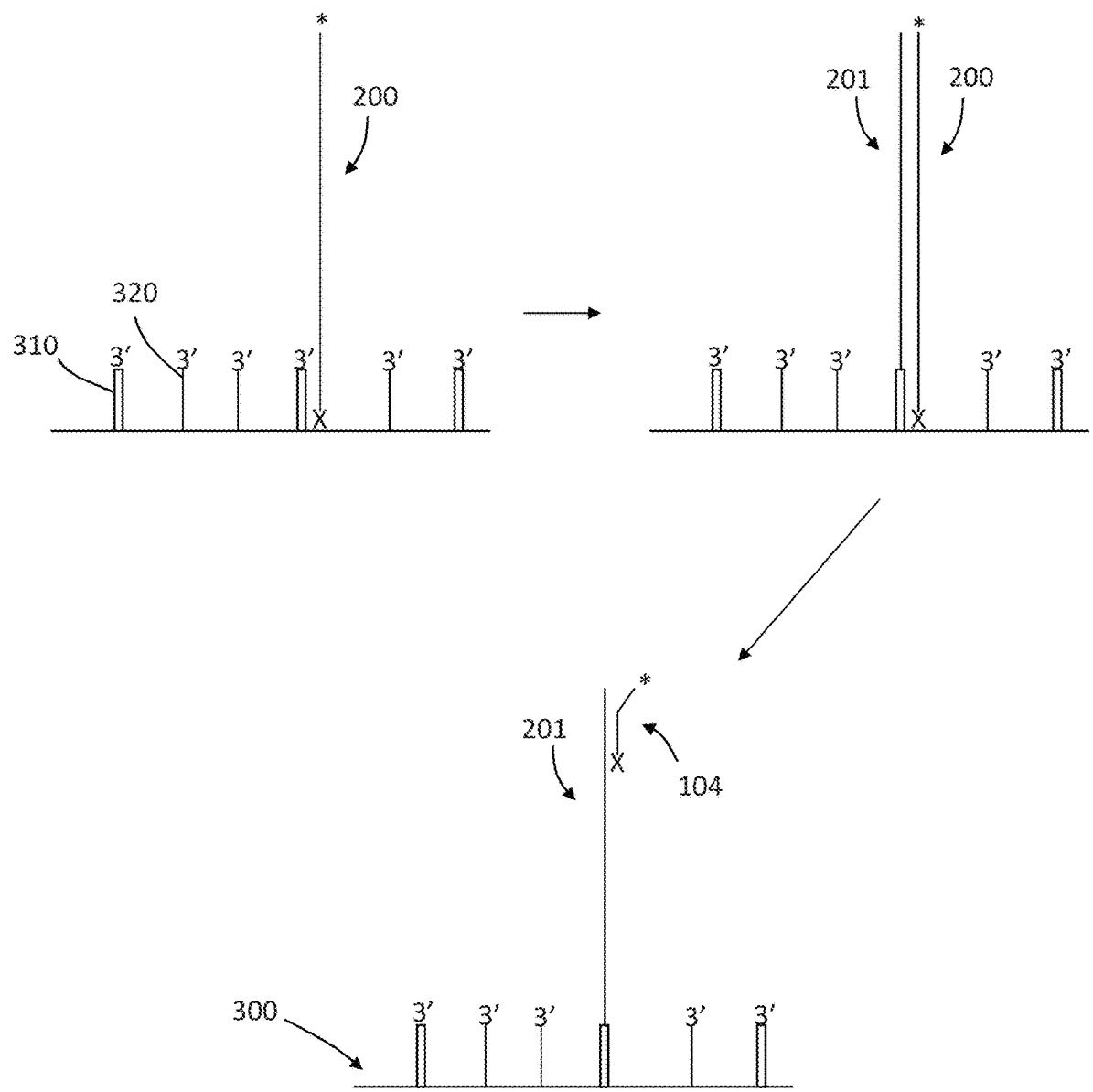
FIG. 5 is a schematic drawing illustrating an embodiment of how 3' end blocking may mitigate index hopping.

Referring now to FIG. 5, a schematic drawing illustrating how blocking of 3' ends (to prevent extension from the blocked 3' end) may mitigate index hopping is shown. The first two panels of FIG. 5 are the same as the first two panels of FIG. 4. As shown in the third panel of FIG. 5, a residual unincorporated (not attached to a target polynucleotide) adapter strand 104 may hybridize to an adapter portion of the copy template strand 201 (for example, the hybridization may occur at the double stranded region of the adapter and the adapter portion of the template polynucleotide). The adapter strand 104 may be from a library different than the library from which the copy template strand 201 is derived. Accordingly, the adapter 104 may have an index tag sequence that is different than the index tag sequence associated with the copy template strand 201. Because the 3' end of the adapter is blocked (indicated by the "X"), the adapter 104 cannot serve as an effective primer to extend and copy the copy template strand 201. However, if extension were permitted (and the 3' end of the unincorporated adapter 104 were not blocked), a copy would be produced in which an incorrect index tag (index tag from adapter 104 from a second library) would be associated with a target polynucleotide from another library (target polynucleotide of template polynucleotide 201 from a first library). In a subsequent round of amplification, an incorrectly indexed polynucleotide could be attached to the surface 300.

Figure 6:
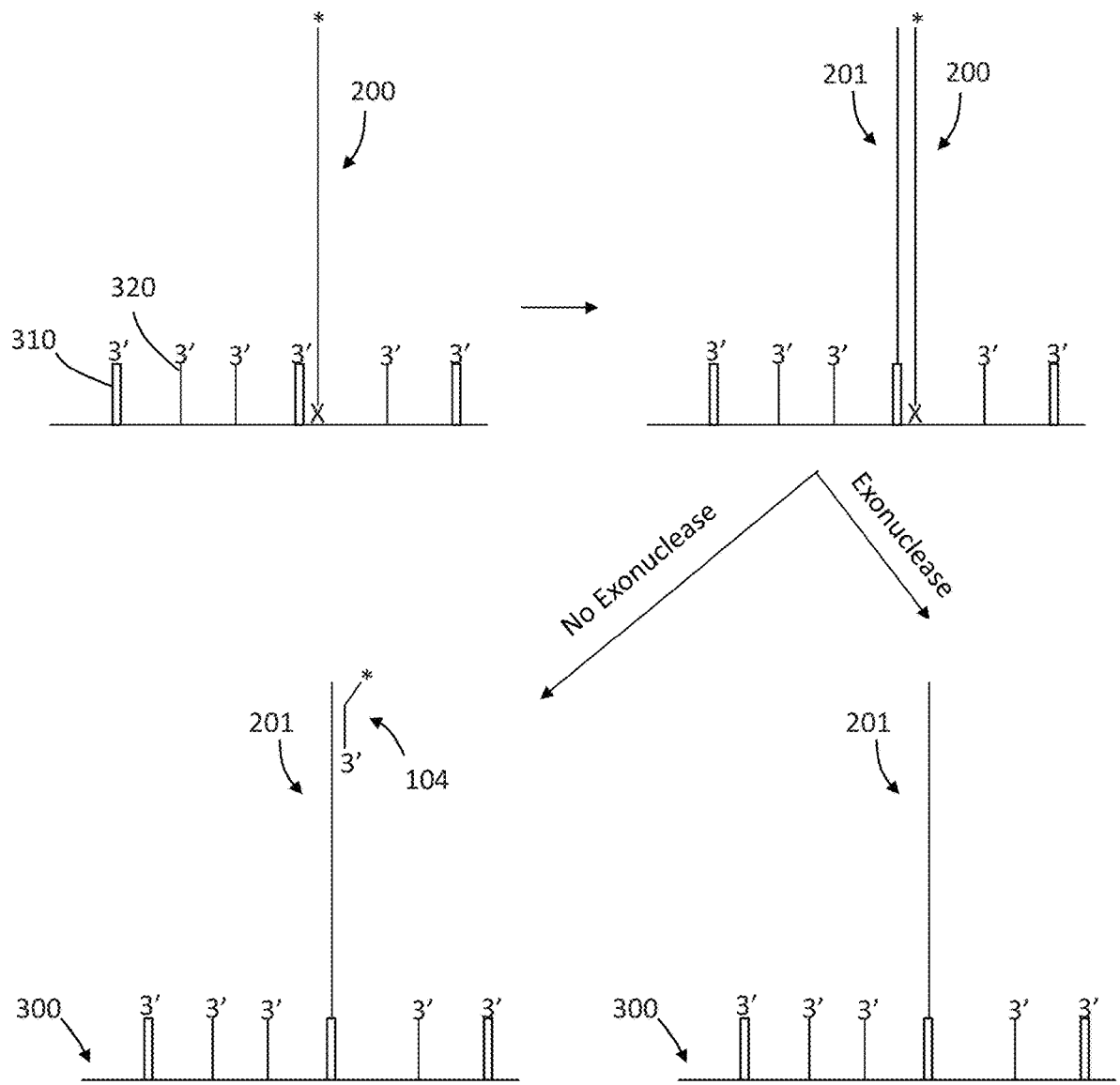
FIG. 6 is a schematic drawing illustrating an embodiment of how exonuclease treatment may mitigate index hopping in accordance with various embodiments described herein.

Referring now to FIG. 6, a schematic drawing illustrating how exonuclease treatment to remove unblocked and unincorporated adapters or adapter strands may mitigate index hopping is shown. The first two panels of FIG. 6 are the same as the first two panels of FIG. 4. As shown in the bottom left panel of FIG. 6, an adapter strand 104 that may result from amplification (e.g., as described regarding FIGS. 1B-F) that was not blocked during a 3' blocking step (e.g., as described regarding FIG. 1G) may hybridize to an adapter portion of the copy template strand 201 (for example, the hybridization may occur at the double stranded region of the adapter and the adapter portion of the template polynucleotide). The adapter strand 104 may be from a library different than the library from which the copy template strand 201 is derived. Accordingly, the adapter strand 104 may have an index tag sequence that is different than the index tag sequence associated with the copy template strand 201. The adapter strand 104 may serve as an effective primer to extend and copy the copy template strand 201. An amplified strand would be produced in which an incorrect index tag (index tag from adapter strand 104 from a second library) would be associated with a target polynucleotide from another library (target polynucleotide of template polynucleotide 201 from a first library). In a subsequent round of amplification, an incorrectly indexed polynucleotide could be attached to the surface 300. However and as illustrated in the bottom right panel of FIG. 6, if the unblocked adapters or adapter strands that may result are digested by exonuclease treatment, the adapter strand is not available to serve as an extension primer and index hoping is mitigated.

Figure 7A:
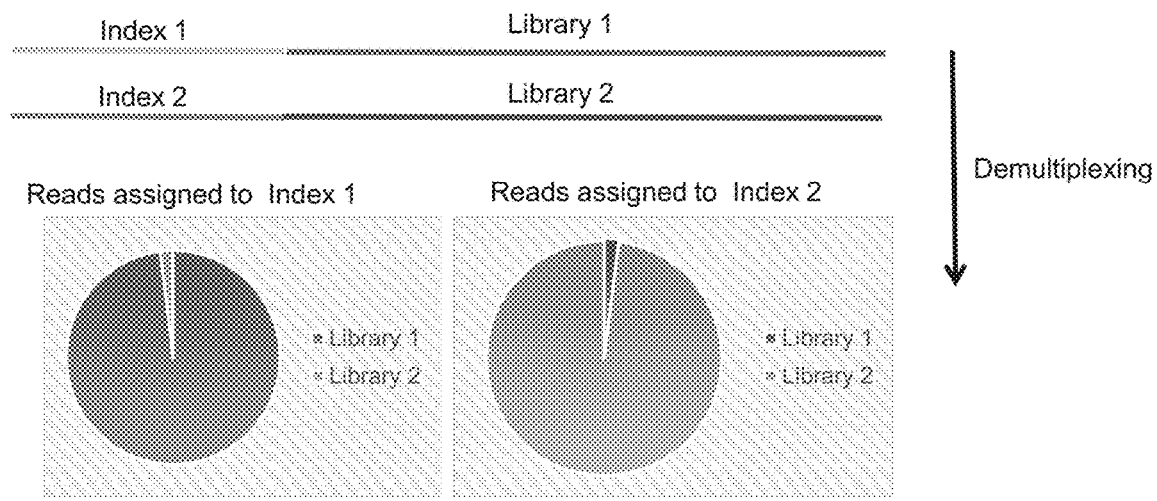
FIGS. 7A and 7B illustrate the nature of the index hopping phenomenon.
Figure 7B:
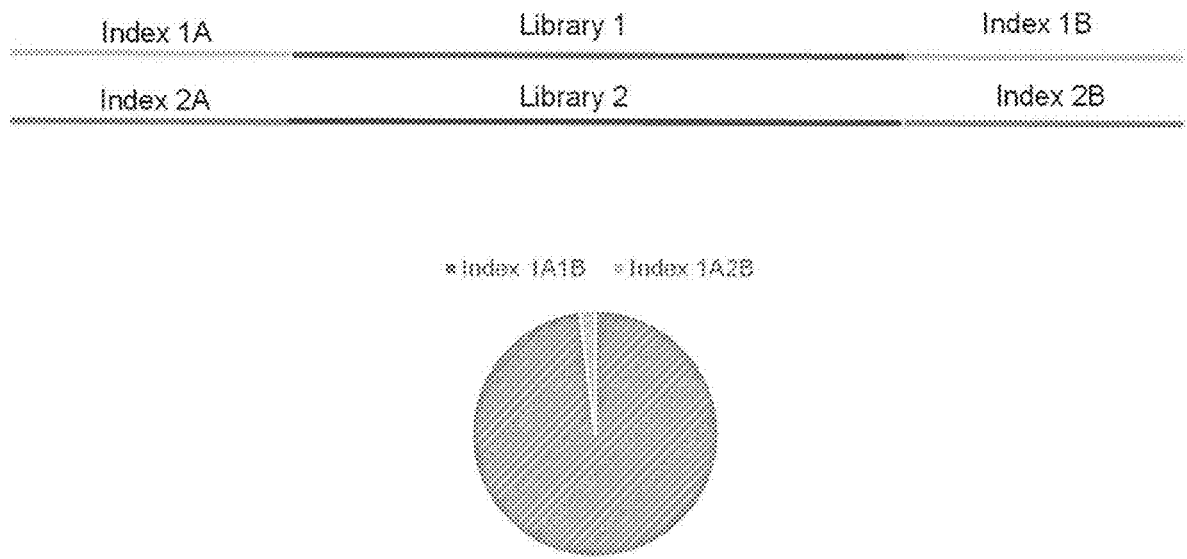

Referring now to FIGS. 7A and 7B, the nature of the index hopping phenomenon is illustrated. FIG. 7A shows how reads from a given sample are incorrectly demultiplexed and mixed with a different sample following demultiplexing.

FIG. 7B demonstrates index hopping in a dual index system, where it leads to unexpected combinations of index tag sequences.

Figures 8A, 8B:
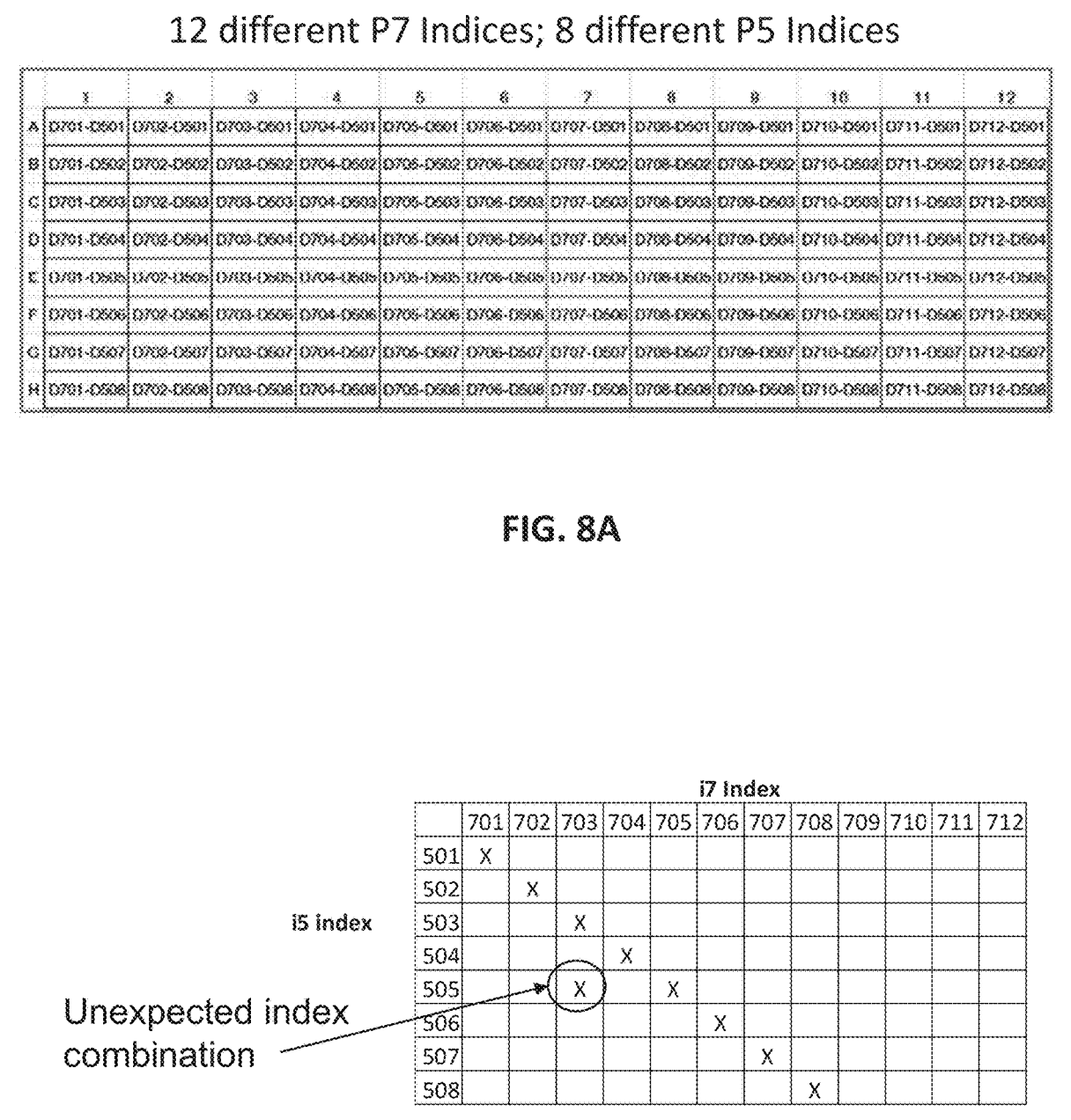

Referring now to FIGS. 8A and 8B, the general approach to measuring the rate of index hopping in a given system is illustrated. FIG. 8A shows an exemplary layout of a dual adapter plate, wherein each individual well of a 96-well plate contains a unique pair of index tag sequences (12 different P7 indices combined with 8 different P5 indices). FIG. 8B shows an experimental setup aimed at measuring the rate of index hopping, wherein 8 unique dual index tag combinations are used (i.e. no P5 index is expected to pair up with more than one P7 index and vice versa). Unexpected combinations of index tags (e.g., D505-D703) are then easily identified as instances of index hopping.

Figure 9A:
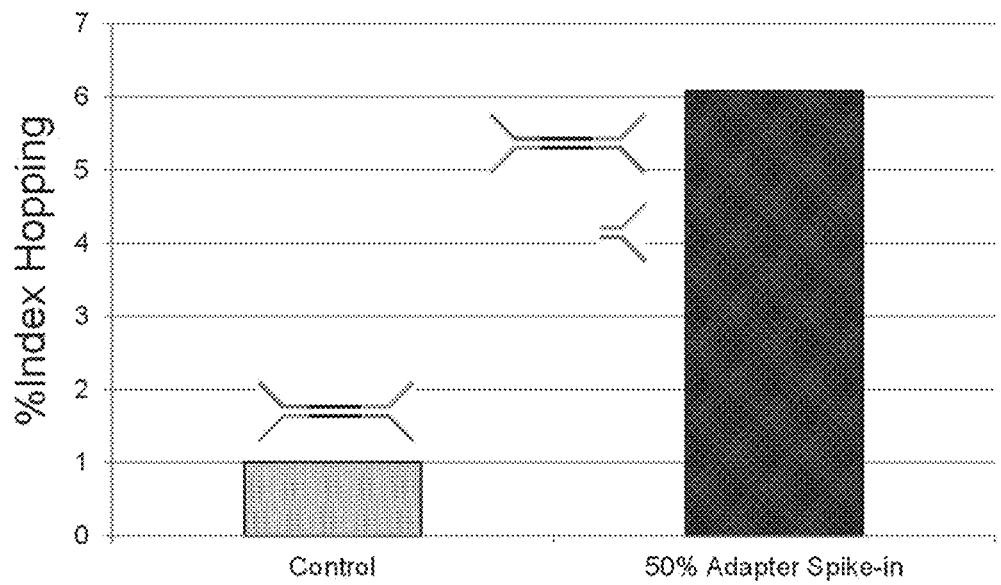
FIGS. 9A and 9B illustrate the effect of unligated adapters on the rate of index hopping.
Figure 9B:
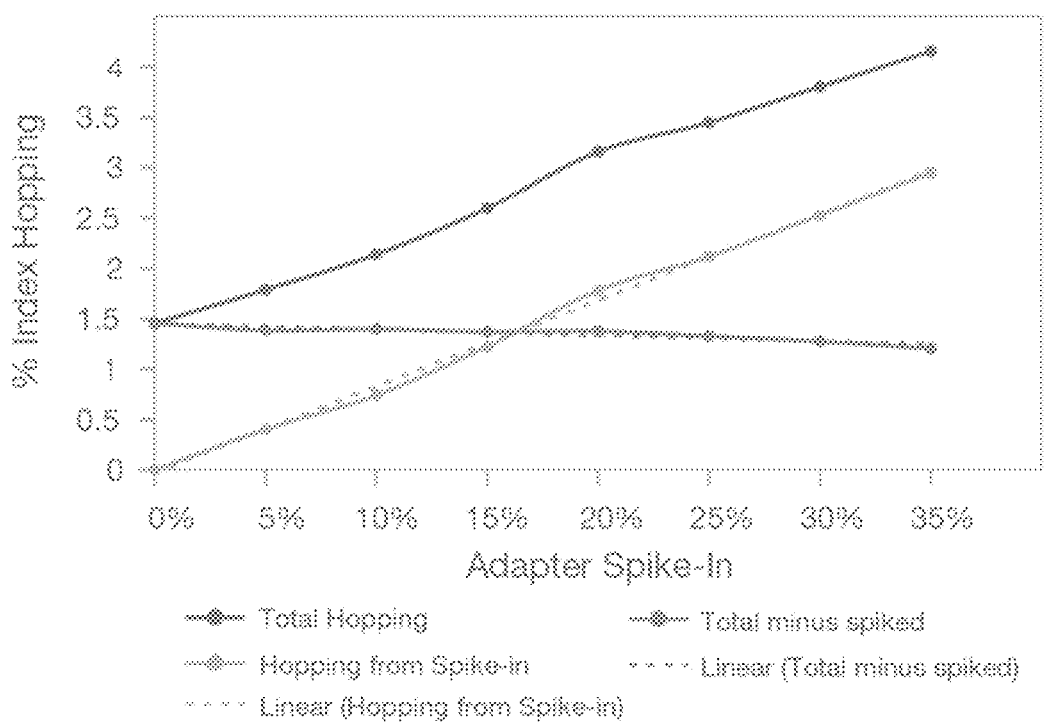

Referring now to FIGS. 9A and 9B, the effect of unligated adapters on the rate of index hopping is illustrated. FIG. 9A shows a 6-fold increase in index hopping associated with a 50% spike-in of free adapters. FIG. 9B shows an approximately linear effect of the free forked adapter on the rate of index hopping within the range tested. The inventors also observed a more pronounced effect of free single-stranded P7 adapters on the rate of index hopping compared to free single-stranded P5 adapters (data not shown).

EXAMPLES

Example 1: Sample Protocol for 3' Blocking of 5' Protected Indexed Libraries

This protocol explains how to perform a 3' blocking treatment of 5' protected DNA libraries, to reduce index hopping. This method is designed to be performed on DNA library pools prior to the denaturation step and subsequent cluster generation using the Illumina HiSeq® 4000 and similar sequencing platforms utilizing patterned flow cells and ExAmp based clustering (e.g., HiSeq® X and NovaSeq®).

Index hopping has been seen to occur where incorrect index sequences are assigned to the insert sequence resulting in sample misassignment. Performing this treatment on DNA sample pools before running on HiSeq® 4000 should reduce the index hopping levels by some level which cannot at this stage be predicted consistently.

Treatment workflow may be considered to involve four steps: (i) produce DNA sample pool; (ii) perform treatment, (iii) cleanup sample and quantify; and (iv) cluster and sequence sample pool.

Consumables/Equipment: Consumables and equipment may be supplied by a sequencing user or manufacture. User supplied consumables may include a DNA library sample pool—30 μl at concentration to be used for denaturation during clustering. The user may also supply freshly prepared 80% ethanol (EtOH).

Table 1 below illustrates some consumables and equipment that may be used.

TABLE 1

| Consumables and Equipment | |
| --- | --- |
| Consumable/Equipment | Supplier |
| Ethanol 200 proof (absolute) for molecular biology | Sigma-Aldrich, Cat #E7023 |
| Magnetic stand-96 | Life Technologies, Cat #AM10027 |
| Vortexer | General lab supplier |
| 96-well thermal cycler (with heated lid) | General lab supplier |

A sequencing manufacturer may supply BMX (Blocking Mix), EMX (Exonuclease Mix), RSB (Resuspension Buffer), and SPB (Sample Purification Beads).

The EMX may include an exonuclease buffer (67 mM Glycine-KOH, 2.5 mM $MgCl_2$, 50 μg/ml BSA) and Lambda Exonuclease (New England Biolabs, Cat #M0262S/L).

The BMX may include a sequencing premix (Tris buffer, sodium chloride, sucrose, magnesium sulfate, EDTA and Tween 20), a ddNTP mix, Pol19 DNA polymerase, and TDT terminal transferase.

The RSB may include a Tris buffer, pH 8.5.

The SPB may include AgenCourt® AMPure® XP beads (Beckman Coulter, Cat #A63880). The SPB should be vortexed before each use. The SPB should be vortexed frequently to make sure that beads are evenly distributed. The SPB should be aspirated and dispensed slowly due to the viscosity of the solution.

Some of the consumables should be stored and prepared as indicated in Table 2 below.

TABLE 2

| Storage and preparation of consumables | | |
| --- | --- | --- |
| Item | Storage | Instructions |
| BMX | −25° C. to −15° C. | Thaw at room temperature, and then place on ice. Return to storage after use. |
| EMX | −25° C. to −15° C. | Thaw at room temperature, and then place on ice. Return to storage after use. |
| RSB | 2° C. to 8° C. | Let stand for 30 min to bring to room temperature. |
| SPB | 2° C. to 8° C. | Let stand for 30 min to bring to room temperature. |

The following EMX program may be saved on the thermal cycler: (i) choose the preheat lid option and set to 100° C.; (ii) 37° C. for 30 mins; (iii) 75° C. for 10 mins; and (iv) hold at 4° C.

The following BMX program may be saved on the thermal cycler: (i) choose the preheat lid option and set to 100° C.; (ii) 38° C. for 20 mins; (iii) 60° C. for 20 mins; and (iv) hold at 4° C.

For the 3' blocking treatment, the samples may be treated as follows: (i) centrifuge BMX at 600×g for 5 seconds; (ii) add 30 μl of 5' protected DNA library sample pool to PCR tube; (iii) add 30 μl BMX to each sample in each PCR tube and then mix thoroughly by pipetting up and down; (iv) incubate by placing on the thermal cycler and running the BMX program. Each tube contains 60 μl.

For the 3' blocking plus exonuclease treatment, the samples may be treated as follows: (i) centrifuge EMX at 600×g for 5 seconds; (ii) add 27 μl of 5' protected DNA library sample pool to PCR tube; (iii) add 5 μl EMX to each sample in each PCR tube and then mix thoroughly by pipetting up and down; (iv) incubate by placing on the thermal cycler and running the EMX program; (v) centrifuge BMX at 600×g for 5 seconds; (vi) add 32 μl BMX directly to each exonuclease reaction in each PCR tube and then mix thoroughly by pipetting up and down; and (vii) incubate by placing on the thermal cycler and running the BMX program. Each tube contains 64 µl.

The treated pooled sample may be cleaned up as follows: (1) vortex SPB until well-dispersed; (2) add 60 µl SPB to each sample treatment tube and mix thoroughly by pipetting up and down; (3) incubate at room temperature for 5 minutes; (4) place on a magnetic stand and wait until the liquid is clear (2-5 minutes); (5) remove and discard all supernatant from each tube; (6) wash 2 times as follows: (a) add 200 µl freshly prepared 80% EtOH to each tube, (b) incubate on the magnetic stand for 30 seconds, and (c) remove and discard all supernatant from each tube; (7) use a 20 µl pipette to remove residual EtOH from each tube; (8) air-dry on the magnetic stand for 5 minutes; (9) add 22.5 µl RSB to each tube; (10) remove from the magnetic stand and then mix thoroughly by pipetting up and down; (11) incubate at room temperature for 2 minutes; (12) place on a magnetic stand and wait until the liquid is clear (2-5 minutes); (13) transfer 20 µl supernatant to a new tube; (14) quantify libraries if required and proceed onto standard clustering for the HiSeq® 4000 platform starting with NaOH denaturation step; and (15) store at −25° C. to −15° C. if not clustering immediately.

Example 2: Reduction of Index Hopping by 3' Blocking of 5' Protected Indexed Libraries The treatment protocol set forth above in Example 1 was applied in combination with the following materials, equipment and methods for clustering and sequencing on Illumina platform.

Experimental conditions: (1) Human 450 bp NA12878 (Coriell Institute) TrueSeq® Nano library generated using 5' protected P5 and P7 primers loaded at 300 pM; (2) HiSeq® X instrument and Illumina SBS chemistry according to manufacturer's instructions; (3) 550 nm ILS v3 flow cell; (4) ExAmp amplification as previously described; and (5) 50% adapter spike-in: free forked adapter from the Illumina dual adapter plate (DAP) spiked into template library prior to denaturation, neutralization, ExAmp mix addition and clustering.

Figure 10:
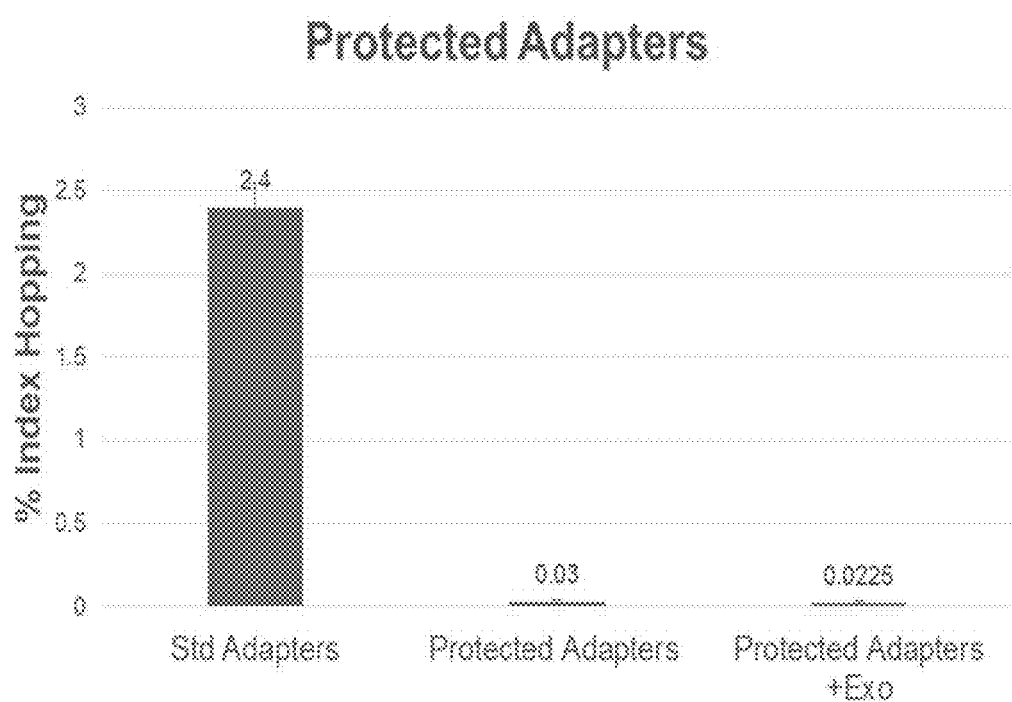
FIG. 10 shows the effect of combined exonuclease and 3' blocking treatment on the rates of index hopping in Illumina TruSeq® Nano (PCR) library preparation work flow, comparing the performance of standard adapters and PCR-protected adapters according to the present invention.

Results of this experiment are summarized in Table 3 below and FIG. 10.

TABLE 3

Reduction of index hopping by PCR protection with 3' blocking

| Library | % Index Hopping |
| --- | --- |
| Standard Adapters | 2.4 |
| 5', 3' Protected Adapters | 0.03 |
| Protected Adapters + Exonuclease | 0.023 |

As illustrated above, index hopping was decreased significantly relative to standard adapters by employing 5' protected and 3' blocked adapters as described herein. Optional exonuclease treatment may have further reduced index hopping.

Any patent, patent application (whether published or not), or other literature referred to herein in hereby incorporated herein in its respective entirety or in part to the extent that it does not conflict with the disclosure presented herein.

In addition to the documents already cited in this application, reference is hereby made to three provisional patent applications identically entitled "Compositions and methods for improving sample identification in indexed nucleic acid libraries" that were filed on the same day as the provisional application to which the present application claims priority (U.S. Provisional Application Nos. 62/488,824, 62/488,825, and 62/488,830, which were filed on Apr. 23, 2017). The entire contents of these applications are also incorporated herein by reference.

It will be apparent to those skilled in the art that various modifications and variations may be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

What is claimed is:

1. A polynucleotide prepared for sequencing, comprising an adapter-target-adapter sequence,
   wherein the adapter sequence comprises a library specific sequence,
   wherein the polynucleotide comprises a double stranded region,
   wherein the 5' ends are each modified to prevent digestion by an enzyme having 5' exonuclease activity,
   wherein the 3' ends are each modified to inhibit digestion by an enzyme having 3' exonuclease activity, to inhibit addition of nucleotides to the 3' ends by an enzyme having polymerase activity, or to inhibit digestion by an enzyme having 3' exonuclease activity and to inhibit addition of nucleotides to the 3' ends by an enzyme having polymerase activity, and
   wherein the 3' ends each comprise a dideoxynucleotide.

2. The polynucleotide according to claim 1, wherein the 5' ends comprise a phosphorothioate bond.

3. The polynucleotide according to claim 1, wherein the 5' ends comprise three phosphorothioate bonds.

4. The polynucleotide according to claim 1, wherein the region that is double stranded comprises the target and at least a portion of the adapter on both ends of the target, and wherein 5' and 3' ends of the polynucleotide in a region of the adapter sequence are single stranded.

5. A method comprising:
   sequencing at least a portion of the polynucleotide of claim 1.

6. A method comprising:
   hybridizing a portion of the 3' end of the polynucleotide according to claim 1 to an oligonucleotide attached to a surface of a substrate, the oligonucleotide having a free 3' end.

7. The method according to claim 6, comprising extending the oligonucleotide attached to the surface of the substrate from the free 3' end by incorporating nucleotides complementary to a sequence of the polynucleotide to produce a copy of the polynucleotide such that the copy is attached to the surface of the substrate.

8. The method according to claim 7, comprising amplifying the copy attached to the surface of the substrate.

9. A composition comprising the polynucleotide according to claim 1.

10. The composition according to claim 9, comprising an exonuclease.

11. The composition according to claim 10, wherein the exonuclease has 3' exonuclease activity.

12. The composition according to claim 10, wherein the exonuclease comprises Exonuclease V.

13. The composition according to claim 9, comprising one or more enzymes having 5' exonuclease activity and 3' exonuclease activity.

14. The composition according to claim 9, comprising amplification reagents.

15. The composition according to claim 9, comprising sequencing reagents.

16. A method comprising:
   incubating an exonuclease with a composition according to claim 9.

17. The method according to claim 16, wherein the exonuclease has 3' exonuclease activity and 5' exonuclease activity.

* * * * *